US011998556B2

(12) United States Patent
Moebius et al.

(10) Patent No.: US 11,998,556 B2
(45) Date of Patent: *Jun. 4, 2024

(54) METHODS OF TREATING PARKINSON'S DISEASE AND/OR LEWY BODY DISEASE OR DISORDER(S)

(71) Applicant: Athira Pharma, Inc., Bothell, WA (US)

(72) Inventors: Hans J. Moebius, Wollerau (CH); Xue Hua, Bothell, WA (US); Kevin Church, Mountlake Terrace, WA (US); William Walker, Kirkland, WA (US); Leen H. Kawas, Lynnwood, WA (US)

(73) Assignee: Athira Pharma, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/814,149

(22) Filed: Jul. 21, 2022

(65) Prior Publication Data

US 2023/0062006 A1 Mar. 2, 2023

(30) Foreign Application Priority Data

Jul. 23, 2021 (WO) ................ PCT/US2021/042974

(51) Int. Cl.
*A61K 31/661* (2006.01)
*A61P 25/16* (2006.01)

(52) U.S. Cl.
CPC ............ *A61K 31/661* (2013.01); *A61P 25/16* (2018.01)

(58) Field of Classification Search
CPC .............................. A61K 31/661; A61P 25/16
See application file for complete search history.

(56) References Cited

U.S. PATENT DOCUMENTS

| | | | | |
|---|---|---|---|---|
| 11,021,514 B2 * | 6/2021 | Kawas | ................ | C07K 5/06078 |
| 2012/0142786 A1 | 6/2012 | Goralczyk et al. | | |
| 2013/0281484 A1 | 10/2013 | Kozikowski et al. | | |
| 2018/0305360 A1 | 10/2018 | Barrow et al. | | |
| 2020/0010504 A1 * | 1/2020 | Kawas | .................... | A61P 25/28 |
| 2020/0054622 A1 | 2/2020 | Braithwaite et al. | | |

FOREIGN PATENT DOCUMENTS

| | | |
|---|---|---|
| WO | 2017210489 A1 | 12/2017 |
| WO | 2019157527 A2 | 8/2019 |

OTHER PUBLICATIONS

Aduhelm™, New Drug Approval, Jun. 7, 2021, 4 pages.
Irwin et al., "Neuropathological and genetic correlates of survival and dementia onset in synucleinopathies: a retrospective analysis," Lancet Neurol, 2017, 16:55-65.
Olichney et al., "Predictive Power of Cognitive Biomarkers in Neurodegenerative Disease Drug Development: Utility of the P300 Event-Related Potential," Neural Plasticity, 2022, Article ID 2104880, 13 pages.
"ATH-1017 Treatment in Subjects with Parkinson's Disease Dementia" ClinicalTrials.gov, ID: NCT04831281, dated Apr. 5, 2021, 7 pages.
Athira Pharma Inc., United States Securities and Exchange Commission, Draft Form S-1, confidentially submitted Jul. 24, 2020, 229 pages.
Athira Pharma Inc., United States Securities and Exchange Commission, Form 8-K, Jun. 21, 2022, 26 pages.
Athira Pharma Inc., United States Securities and Exchange Commission, Form 8-K, Oct. 18, 2021, 7 pages.
Athira Pharma Inc., United States Securities and Exchange Commission, Form S-1, Aug. 26, 2020, 351 pages.
Athira Pharma Press Release, "Athira Pharma Presents Data from ACT-AD Phase 2 Proof-of-Concept Clinical Study of Fosgonimeton in Mild-to-Moderate Alzheimer's Patients at the Alzheimer's Patients at the Alzheimer's Association International Conference 2022," Aug. 3, 2022, 3 pages.
Athira Pharma Press Release, Retrieved from the internet: https://www.athira.com/athira-pharma-announces-leadership-changes//, "Athira Pharma Announces Leadership Changes," Oct. 21, 2021, 2 pages.
Benoist et al., "The Procognitive and Synaptogenic Effects of Angiotensin IV-Derived Peptides are Dependent on Activation of the Hepatocyte Growth Factor/c-Met System," The Journal of Pharmacology and Experimental Therapeutics, 351:390-402, Nov. 2014.
Cummings et al., "Alzheimer's Disease Drug Development Pipeline: 2018," Alzheimer's & Dementia: Transl Res & Clin Interventions, 2018, 4:195-214.
File History of U.S. Appl. No. 17/864,702, filed Jul. 14, 2022, Inventors: Hans J. Moebius et al.
Hua et al., "Safety, Tolerability, Pharmacokinetics, and Pharmacodynamics of the Positive Modulator of HGF/MET, Fosgonimeton, in Healthy Volunteers and Subjects with Alzheimer's Disease: Randomized, Placebo-Controlled, Double-Blind, Phase I Clinical Trial," J Alzheimer's Disease, 2022, 86:1399-1413.
International Search Report and Written Opinion received in PCT/US2021/042071, dated Oct. 26, 2021, Applicant: Athira Pharma, Inc.; 9 pages.
International Search Report and Written Opinion received in PCT/US2021/042974, dated Dec. 30, 2021, Applicant: Athira Pharma, Inc.; 16 pages.
International Search Report and Written Opinion received in PCT/US2022/034386, dated Oct. 5, 2022, Applicant: Athira Pharma, Inc.; 9 pages.
International Search Report and Written Opinion received in PCT/US2022/074021, dated Oct. 4, 2022, Applicant: Athira Pharma, Inc.; 11 pages.
Kawas et al., "Development of Angiotensin IV Analogs as Hepatocyte Growth Factor/Met Modifiers," The Journal of Pharmacology and Experimental Therapeutics, vol. 340, No. 3, 2012, pp. 539-548.
Kawas et al., "Mimics of the Dimerization Domain of Hepatocyte Growth Factor Exhibit Anti-Met and Anticancer Activity," The Journal of Pharmacology and Experimental Therapeutics, vol. 339, No. 2, Aug. 2011, pp. 509-518 and supplemental figures 1-3 and Erratum.

(Continued)

*Primary Examiner* — Timothy R Rozof
(74) *Attorney, Agent, or Firm* — McNeill Baur PLLC

(57) ABSTRACT

The present disclosure relates to a method of treating Parkinson's Disease and/or Lewy body disease or disorder(s), including Parkinson's disease dementia and dementia with Lewy bodies, comprising administering to a subject ATH-1017.

22 Claims, No Drawings

(56) References Cited

OTHER PUBLICATIONS

Kawas et al., "Nanoscale mapping of the Met receptor on hippocampal neurons by AFM and confocal microscopy," Nanomedicine: Nanotechnology, Biology and Medicine, vol. 9, Issue 3, Apr. 2013, pp. 428-438.
Kokras et al., "Acetyl Cholinesterase Inhibitors and Cell-Derived Peripheral Inflammatory Cytokines in Early Stages of Alzheimer's Disease," J Clin Psychopharmacology, 2018, 38(2): 1-6.
Kulisevsky et al., "Cognitive Impairment in Parkinson's Disease: Tools for Diagnosis and Assessment," Movement Disorders, 2009, 24(8): 1103-1110.
Miller et al., "Gender Differences in Parkinson's Disease: Clinical Characteristics and Cognition," Movement Disorders, 2010, 25(16): 2695-2703.
Moebius et al., "HGF/MET Receptor Agonist NDX-1017 Translational Phase 1a and b Results," Athira Pharma Presentation, Dec. 2019, 24 pages.
Pasricha, "Athira Pharma's shares plunge after Bothell company's CEO placed on leave," Jun. 18, 2021, The Seattle Times, pp. 1-3.
PubChem ID No. CID-156596375, Fosgonimeton, dated Sep. 16, 2021, 12 pages.
PubPeer, Jul. 13, 2021 [online]. Retrieved from the internet: https://pubpeer.com/publications/01199F548BE82EE44C7D395568982B, "Development of angiotensin IV analogs as hepatocyte growth factor/Met modifiers," pp. 1-5.
PubPeer, Jul. 13, 2021 [online]. Retrieved from the internet: https://pubpeer.com/publications/36F84FDB31C718C8CF8F52C717D15C, "Nanoscale mapping of the Met receptor on hippocampal neurons by AFM and confocal microscopy," pp. 1-8.
PubPeer, Jul. 13, 2021 [online]. Retrieved from the internet: https://pubpeer.com/publications/4D8EFBD349D1A779627479FB694F7C, "Evaluation of metabolically stabilized angiotensin IV analogs as procognitive/antidementia agents," pp. 1-2.
PubPeer, Jul. 13, 2021 [online]. Retrieved from the internet: https://pubpeer.com/publications/51C554512CE22267B2E62172DF3DDE, "Mimics of the dimerization domain of hepatocyte growth factor exhibit anti-Met and anticancer activity," pp. 1-8.
PubPeer, Jul. 13, 2021 [online]. Retrieved from the internet: https://pubpeer.com/publications/56408F27C1C94294C69E8466C44C2B, "Plasma phospholipids identify antecedent memory impairment in older adults," pp. 1-3.
PubPeer, Jul. 13, 2021 [online]. Retrieved from the internet: https://pubpeer.com/publications/D5375331091A7EF887CDC02B813ACA, "The Procognitive and Synaptogenic Effects of Angiotensin IV-Derived Peptides are Dependent on Activation of the Hepatocyte Growth Factor/c-Met System," pp. 1-6.
PubPeer, Jul. 13, 2021 [online]. Retrieved from the internet: https://pubpeer.com/publications/D803673763EF5404FAE8CC546CC028, "Hepatocyte growth factor mimetic protects lateral line hair cells from aminoglycoside exposure," pp. 1-2.
PubPeer, Jun. 16, 2021 [online]. Retrieved from the internet: https://pubpeer.com/search?q=Kawas, pp. 1-2.
Sarikaya et al., "Evaluation of Cognitive Functions in Parkinson's Patients without Dementia with Auditory Event Related Potential (P300)," J Psychiatry Neurological Sci, 2014, 27:132-137.
Schneider, "For Better Science," Jun. 15, 2021, 32 pages.
Sun et al., "AngIV-Analog Dihexa Rescues Cognitive Impairment and Recovers Memory in the APP/PS1 Mouse via the PI3K/AKT Signaling Pathway," Brain Sciences, 2021, 11:1487, 13 pages.
"ATH-1017 Treatment in Subjects with Parkinson's Disease Dementia or Dementia with Lewy Bodies (Shape Trial)" ClinicalTrials gov, ID: NCT04831281, dated Jul. 24, 2023, 11 pages.
Aduhelm™, Prescibing Information, 2021, 22 pages.
Athira Pharma Press Release, "Athira Pharma Provides 2023 Pipeline Outlook," Jan. 5, 2023, 2 pages.
Leuzy et al., "Blood-based biomarkers for Alzheimer's disease," EMBO Mol Med, 2022, 14:e14408, 15 pages.
Moebius et al., Fosgonimeton Provides Congruent Improvements on Neurodegeneration Biomarkers, Significantly Correlating with Composite Clinical Scores of Cognition and Function in Alzheimer's Disease, Apr. 22-27, 2023, Boston, MA, Presentation at the 75th AAN Annual Meeting, 16 pages.
Moebuis et al., "ACT-AD: Fosgonimeton in Mild-to-Moderate Alzhemier's Disease—First Results of a Randomized, Placebo-Controlled, 26-Week, Phase 2 Proof-of-Concept Trial," Presentation at AAIC 2022, 13 pages.
Cummings, et al., "Treatment Combinations for Alzheimer's Disease: Current and Future Pharmacotherapy Options", Journal of Alzheimer's Disease 67 (2019) 779-794 (16 pgs).
Guo, et al., "Memantine, Donepezil, or Combination Therapy—What is the best therapy for Alzheimer's Disease? A Network Meta-Analysis", Brain and Behavior, 2020, (13 pgs).
Akimoto, M., et al., "Hepatocyte growth factor as an enhancer of NMDA currents andsynaptic plasticity in the hippocampus", Neuroscience 128, 2004, 155-162 (8 pgs).
Akita, H., et al., "Hepatocyte growth factor improves synaptic localization of the NMDA receptor and intracellular signaling after excitotoxic injury in culturedhippocampal neurons", Expimental Neurology 210, 2008, 83-94 (12 pgs).
Alberts B., et al., "General Principles of Cell Communication", Molecular Biology of the Cell, 4th edition, New York: GarlandScience, 2002. Available from:https://www.ncbi.nlm.nih.gov/books/NBK26813/. Accessed Mar. 23, 2023. (19 pgs).
Ally, B.A., et al., "The P300 component in patients with Alzheimer's disease and their biological children", Biological Psychology 72, 2006 180-7 (8 pgs).
Annonymous, "2022 Alzheimer's disease facts and figures", Alzheimers and Dementia 2022, 18, 700-789 (90 pgs).
Annonymous, "Athira Pharma Highlights Therapeutic Potential of Fosgonimeton in Presentation of Additional Biomarker Data in Mild-to-Moderate Alzheimer's Disease Patients from ACT-AD Phase 2 Study atCTAD Conference", Nov. 29, 2022, 2 pages.
Annonymous, "Form S-1 Registration Statement of Athira Pharma, Inc.," filed with United States Securities and Exchange Commission Sep. 14, 2020, 285 pages.
Annonymous, "WHO Drug Information", vol. 35, No. 2, 2021, 4 pages.
Armada-Moreira, A., et al., "Going the Extra (Synaptic) Mile: Excitotoxicity as the Road Toward Neurodegenerative Diseases", Frontiers in Cellular Neuroscience 14, 90, 2020 (27 pgs.).
Arneson, D., et al., "Shared mechanisms among neurodegenerative diseases: from genetic factors to gene networks", Journals of Genetics 97, 2018, 795-806 (12 pgs.).
Asomugha, C.O., et al., "ACh receptors link two signaling pathways to neuroprotection against glutamate-induced excitotoxicity in isolated RGCs", J Neurochem112, 2010, 214-26 (25 pgs.).
Baiardi, S., et al., "Diagnostic value of plasma p-tau181, NfL, and GFAP in a clinical setting cohort of prevalent neurodegenerative dementias", Alzheimer's Research & Therapy 14, 153, 2022 (12 pgs).
Batista, C.R.A., et al., "Lipopolysaccharide-Induced Neuroinflammation as a Bridge to Understand Neurodegeneration", Int. J. Mol. Sci 20, 2293, 2019, (31 pgs).
Chen, Y., et al., "A non-transgenic mouse model (ICV-STZ mouse) of Alzheimer's disease: similarities to and differences from the transgenic model (3xTg-ADmouse)", Mol Neurobiol 47, 2013, 711-25 (15 pgs).
Chitnis, T et al., "CNS inflammation and neurodegeneration", J Clin Invest 127, 2017, 3577-3587 (11 pgs).
Cummings, J., et al., "Advances in designs for Alzheimer's disease clinical trials", Am J Neurodegener Dis 2012, 1 (3):205-216 (12 pgs).
Das, J.R., et al., "Additive protective effects of donepezil and nicotine againsts alsolinol-induced cytotoxicity in SH-SY5Y cells", Neurotox Res 16, 2009, 194-204 (11 pgs.).

(56) References Cited

OTHER PUBLICATIONS

De Strooper, B., et al., "The Cellular Phase of Alzheimer's Disease", Cell 164, 2016, 603-15 (13 pgs.).
Desole, C., et al., "HGF and MET: From Brain Development to Neurological Disorders", Front Cell Dev Biol 9, 683609, 2021 (21 pgs.).
Eagleson, K.L, et al., "Distinct intracellular signaling mediates c-MET regulation of dendritic growth and synaptogenesis", Developmental Neurobiology 76, 2016, 1160-81 (22 pgs.).
Faes, S., et al., "PI3K and AKT: Unfaithful Partners in Cancer", Int J Mol Sci 16, 2015, 21138-21152 (15 pgs.).
Funakoshi, H., et al. "Hepatocyte Growth Factor (HGF): Neurotrophicfunctions and therapeutic implications for neuronal injury/diseases", Current Signal Transduction Therapy, 6, 2011, 156-167 (12 pgs).
Funakoshi, H., et al., "Hepatocyte growth factor: from diagnosis toclinical applications", Clin Chim Acta 327, 2003, 1-23 (23 pgs).
Gao, B.L., et al., "Neuroprotective effects of donepezil against Aβ25-35-inducedneurotoxicity", Eur J Med Res 27, 219, 2022 (8pgs).
Götze, K., et al., "Plasma neurofilament light chain in memory clinic practice:Evidence from a real-life study", Neurobiol Dis. 176, 105937, 2023 (7 pgs).
He, F., et al., "HGF protects cultured cortical neurons against hypoxia/reoxygenationinduced cell injury via ERK1/2 and PI-3K/Akt pathways", Colloids Surf B Biointerfaces 61, 2008, 290-297 (8 pgs.).
Hewett, S.J., et al., "Interleukin-1β in Central Nervous System Injury and Repair", Eur J Neurodegener Dis 1, 2012, 195-211 (21 pgs.).
Higgins, J. "Prodrugs in Drug Discovery", ACS Webinars, Nov. 19, 2015 (27 pgs).
Hua, X., et al., "Safety, Tolerability, Pharmacokinetics, and Pharmacodynamics of the Positive Modulator of HGF/MET, Fosgonimeton, in Healthy Volunteers and Subjects with Alzheimer's Disease: Randomized, Placebo-Controlled, Double-Blind, Phase I Clinical Trial", J Alzheimers Dis 86, 2022, 1399-1413 (15 pgs).
Hwang, J., et al., "Microglia signaling as a target of donepezil", Neuropharmacology 58, 2010, 1122-1129 (8 pgs).
Hynd, M.R., et al., "Glutamate-mediated excitotoxicity and neurodegeneration in Alzheimer's disease", Neurochem Int 45, 2004, 583-595 (13 pgs).
Ishihara, N., et al., "Inhibition of apoptosis-inducing factor translocation is involved in protective effects of hepatocyte growth factor against excitotoxic cell death incultured hippocampal neurons", Journal of Neurochemistry 95, 2005, 1277-1286 (10 pgs).
Ito, K., et al., "Artificial human Met agonists based on macrocycle scaffolds", Nat Commun 11, 2015, 63-73 (11 pgs).
Jack Jr, C.R., et al., "A/T/N: An unbiased descriptive classification scheme for Alzheimer disease biomarkers", Neurology 87, 2016, 539-547 (9 pgs).
Jack Jr, C.R., et al., "NIA-AA Research Framework: Toward a biological definition ofAlzheimer's disease", Alzheimer's & Dementia 14, 2018, 535-562 (28 pgs).
Jayaraman, A., et al., "TNF-mediated neuroinflammation is linked to neuronal necroptosis in Alzheimer's disease hippocampus", Acta Neuropathol Commun9, 159, 2021 (21 pgs).
Jeong, J., "EEG dynamics in patients with Alzheimer's disease", Clin Neurophysiol 115, 2004, 1490-1505 (16 pgs).
Jia, Y., et al., "HGF Mediates Clinical-Grade Human Umbilical Cord-Derived Mesenchymal Stem Cells Improved Functional Recovery in a Senescence-Accelerated Mouse Model of Alzheimer's Disease", Adv Sci 7, 1903809, 2020, 17 pgs.
Johnston, J.L., et al., "Fosgonimeton, a Novel Positive Modulator of the HGF/MET System, Promotes Neurotrophic and Procognitive Effects in Models of Dementia", Neurotherapeutics, 2022, Available from:https://pubmed.ncbi.nlm.nih.gov/36538176/. Accessed Mar. 23, 2023 (21 pgs).
Kennedy, R., et al., "Association of Concomitant Use of Cholinesterase Inhibitors or Memantine With Cognitive Decline in Alzheimer Clinical Trials A Meta-analysis", JAMA Network Open, 2018, Downloaded From: https://jamanetwork.com/ on May 23, 2023 (10 pgs).
Knopman, D.S., et al., "Alzheimer disease", Nat Rev Dis Primers 7, 33, 2021 (47 pgs).
Koffie, R.M., et al., "Alzheimer's disease: synapses gone cold", Molecular Neurodegeneration 6, 63, 2011 (9 pgs).
Koike, H., et al., "Prevention of onset of Parkinson's disease by in vivo gene transfer of human hepatocyte growth factor in rodent model: a model of gene therapy for Parkinson's disease", Gene Ther 13, 2006, 1639-1644 (6 pgs).
Kraska, A., et al., "In Vivo Cross-sectional Characterization of Cerebral Alterations Induced by Intracerebroventricular Administration of Streptozotocin", PLOS One 7, e46196, 2012 (9 pgs).
Kulczynska-Przybik, A., et al. "Cerebrospinal Fluid and Blood CX3CL1 as a Potential Biomarker in Early Diagnosis and Prognosis of Dementia", Curr Alzheimer Res 17, 2020, 709-721 (13 pgs.).
LeBlanc, C. A., "The Role of Apoptotic Pathways in Alzheimer's Disease Neurodegeneration and Cell Death", Current Alzheimer Research 2, 2005, 389-402 (14 pgs.).
Lewczuk, P., et al., "Plasma neurofilament light as a potential biomarker of neurodegeneration in Alzheimer's disease", Alzheimers Res Ther 10, 71, 2018 (10 pgs).
Liu, J., et al., "The Role of NMDA Receptors in Alzheimer's Disease", Front Neurosci 8, 43, 2019 (22 pgs).
Liu, X.S., et al., "Human umbilical cord mesenchymal stem cells infected with adenovirus expressing HGF promote regeneration of damaged neuron cells in a Parkinson's disease model", Biomed Research International, 2014, Article ID: 909657 (7 pgs).
Lloret, A., et al., "Amyloid-β toxicity and tau hyperphosphorylation are linked via RCAN1 in Alzheimer's disease", Journal of Alzheimer's disease, JAD 27, 2011, 701-9 (9 pgs.).
Maina, F., et al., "Hepatocyte growth factor, a versatile signal for developing neurons", Nature Neuroscience 2, 1999, 213-217 (5 pgs).
Mattsson, N., et al., "Association Between Longitudinal Plasma Neurofilament Light and Neurodegeneration in Patients With Alzheimer Disease", JAMA Neurol 76, 2019, 791-799 (9 pgs).
McKhann G.M., et al., "The diagnosis of dementia due to Alzheimer's disease: recommendations from the National Institute on Aging-Alzheimer's Association workgroups on diagnostic guidelines for Alzheimer's disease", Alzheimers Dement 7, 2011, 263-9 (11 pgs).
Mehta, C.R., et al., "Adaptive increase in sample size when interim results are promising: A practical guide with examples", Statist. Med., 30, 2000, 3267-3284 (20 pgs).
Meraz-Rios, M.A., et al., "Inflammatory process in Alzheimer's Disease", Front Integr Neurosci 7 (article 59), 2013, 1-15 (15 pgs).
Moebius et al., "ACT-AD: Fosgonimeton in Mild-to-Moderate Alzheimer's Disease—First Results of a Randomized, Placebo-Controlled, 26-Week, Phase 2 Proof-of-Concept Trial", 2022 (13 pgs).
Moebius, H., et al., "Fosgonimeton Provides Congruent Benefit on Diverse Biomarkers of Neurodegeneration, Significantly Correlating With a Composite Clinical Score of Cognition and Function in Alzheimer's Disease", 2022 (2 pgs).
Molnarfi, N., et al., "Hepatocyte growth factor: A regulator of inflammation and autoimmunity", Autoimmun Rev 14, 2015, 293-303 (12 pgs).
Muir, J.L., "Acetylcholine, aging, and Alzheimer's disease", Pharmacol Biochem Behav 56, 1997, 687-696 (10 pgs).
Nazem, A., et al., "Rodent models of neuroinflammation for Alzheimer's disease", J Neuroinflammation 12, 74, 2015 (15 pgs).
Noh, M.Y., et al., "Neuroprotective effects of donepezil through inhibition of GSK-3activity in amyloid-beta-induced neuronal cell death", J Neurochem 108, 2009, 1116-1125 (10 pgs).
Okaichi, H., et al., "Scopolamine impairs both working and reference memory in rats: a replication and extension", Pharmacol Biochem Behav 34, 1989, 599-602 (4 pgs).
Olichney, J.M., et al., "Predictive Power of Cognitive Biomarkers in Neurodegenerative Disease Drug Development: Utility of the P300 Event-Related Potential", Neural Plast 2104880, 2022 (3 pgs).

(56) References Cited

OTHER PUBLICATIONS

Osborn, L.M., et al., "Astrogliosis: An integral player in the pathogenesis of Alzheimer's disease", Prog Neurobiol 144, 2016, 121-141 (21 pgs).
Park, SA., et al., "Promising Blood Biomarkers for Clinical Use in Alzheimer's Disease: A Focused Update", J Clin Neurol 18, 2022, 401-409 (9 pgs).
Pasqualetti, G., et al., "The Role of Neuroinflammation in Dementias", Curr Neurol Neurosci Rep 15, 17, 2015 (11 pgs).
Ramesh, V., et al., "Biphasic responses in cell signalling: A unified approach", bioRxiv, 2023 (28 pgs).
Raz, L., et al., "The neuropathology and cerebrovascular mechanisms of dementia", J Cereb Blood Flow Metab. 1, 2016, 172-186 (15 pgs).
Riekkinen, P., et al., "Effects of scopolamine infusions into the anterior and posteriorcingulate on passive avoidance and water maze navigation", Brain Res 685, 46-54 (9 pgs).
Salvadó G., et al., "Specific associations between plasma biomarkers and post-mortem amyloid plaque and neurofibrillary tau tangle loads", medRxiv, 2022 (38 pgs).
Selkoe, D. J., "Alzheimer's disease is a synaptic failure", Science 298, 2002, 789-91 (3 pgs.).
Serrano-Pozo, A., et al., "Neuropathological alterations in Alzheimer disease", Cold Spring Harb Perspect Med 1, a006189, 2011 (24 pgs).
Shang, J., et al., "Strong neurogenesis, angiogenesis, synaptogenesis, and antifibrosis of hepatocyte growth factor in rats brain after transient middle cerebral arteryocclusion", J Neurosci Res 89, 2011, 86-95 (10 pgs.).
Shen, H., et al., "Neuroprotection by donepezil against glutamate excitotoxicity involves stimulation of alpha7 nicotinic receptors and internalization of NMDA receptors", Br J Pharmacol 161, 2010, 127-39 (13 pgs.).
Shulman, Y., et al., "ATP binding to synaspsin IIa regulates usage and clustering of vesicles in terminals of hippocampal neurons", J Neurosci 35, 2015, 985-98 (14 pgs.).
Stancu, I.C, et al., "Models of β-Amyloid Induced Tau-Pathology: The Long and 'Folded' Road to Understand the Mechanism", Molecular Neurodegeneration, 9, 51, 2014 (14 pgs).
Stoiljkovic, M., et al., "Therapy for Alzheimer's disease: Missing targets and functional markers?", Ageing Res Rev 68, 101318, 2021 (15 pgs).
Sun, W., et al., "Overexpression of HGF retards disease progression and prolongs lifespan in a transgenic mouse model of ALS", J Neurosci. 22, 6537-6548 2002 (12 pgs.).
Takada-Takatori, Y., et al., "Acetylcholinesterase inhibitors used in treatment of Alzheimer's disease prevent glutamate neurotoxicity via nicotinic acetylcholine receptors and phosphatidylinositol 3-kinase cascade", Neuropharmacology 51, 2006, 474-486 (13 pgs.).
Takada-Takatori, Y., et al., "Mechanism of neuroprotection by donepezil pretreatment in rat cortical neurons chronically treated with donepezil", J Neurosci Res86, 2008, 3575-3583 (9 pgs.).
Takeuchi, D., et al., "Alleviation of Aβ-induced cognitive impairment by ultrasound-mediated gene transfer of HGF in a mouse model", Gene Ther15, 2008, 561-571 (11 pgs.).
Tancredi, V., et al., "The inhibitory effects of interleukin-6 on synaptic plasticity in the rat hippocampus are associated with an inhibition of mitogen-activated protein kinase ERK", J Neurochem 75, 2000, 634-43 (10 pgs).
Thomas, A., et al., "Donepezil, rivastigmine, and vitamin E in Alzheimer disease: a combined P300 event-related potentials/neuropsychologic evaluation over 6 months", Clin Neuropharmacol 24, 2001, 31-42 (12 pgs.).
Tulasne, D., et al., "The shadow of death on the MET tyrosine kinase receptor", Cell Death Differ 15, 2008, 427-34 (8 pgs.).
Tyndall, S.J., et al., "Hepatocyte growth factor-induced enhancement of dendritic branching is blocked by inhibitors of N-methyl-D-aspartate receptors and calcium/calmodulin-dependent kinases", J Neurosci Res 85, 2007, 2343-2351 (9 pgs.).
Wang, T., et al., "Hepatocyte growth factor acts as a mitogen and chemoattractant for postnatal subventricular zone-olfactory bulb neurogenesis", Mol Cell Neurosci48, 2011, 38-50 (24 pgs.).
Wilczynska, K, et al., "Diagnostic Utility of Selected Serum Dementia Biomarkers: Amyloid β-40, Amyloid β-42, Tau Protein, and YKL-40: A Review", J Clin Med 9, 3452, 2020 (26 pgs).
Xiao, G.H., et al., "Anti-apoptotic signaling by hepatocyte growth factor/Met via the phosphatidylinositol 3-kinase/Akt and mitogen-activated protein kinase pathways", Proc Natl Acad Sci U S A 98, 2001, 247-52 (6 pgs.).
Yaari, R., et al., "Alzheimer's disease clinical trials: past failures and future opportunities", Clin. Invest. (Lond.) 2015 5 (3), 297-309 (13 pgs.).
Yuan, A., et al., "Neurofilament Proteins as Biomarkers to Monitor Neurological Diseases and the Efficacy of Therapies", Front Neurosci 15, 689938, 2021 (28 pgs).
Yuan, J., et al., "Severity Distribution of Alzheimer's Disease Dementia and Mild Cognitive Impairment in the Framingham Heart Study",. J Alzheimers Dis79, 2021, 807-817 (11 pgs.).
Moebius, et al., "The Case for a Novel Therapeutic Approach to Dementia: Small Molecule Hepatocyte Growth Factor (HGF/MET) Positive Modulators", Journal of Alzheimer's Disease 92, (2023), pp. 1-12 (12 pgs).
Sun, et al., "AngIV-Analog Dihexa Rescues Cognitive Impairment and Recovers Memory in the APP/PS1 Mouse via the PI3K/AKT Signaling Pathway", Brain Sci. 2021, 11, 1487 (13 pgs).
Annonymous, "ATH-1017 Treatment in Subjects with Parkinson's Disease Dementia or Dementia with Lewy Bodies (Shape Trial)" ClinicalTrials.gov, ID: NCT04831281, dated Jul. 24, 2023 (11 pgs).
Athira Pharma Press Release, "Athira Pharma Provides 2023 Pipeline Outlook," Jan. 5, 2023, (2 pgs).
Athira Pharma Press Release, "Athira Pharma Announces Encouraging Results from Shape Phase 2 Clinical Trial of Fosgonimeton for the Treatment of Parkinson's Disease Dementia and Dementia with Lewy Bodies", Dec. 12, 2023 (2 pgs).
Non-Final Office Action in U.S. Appl. No. 17/864,702, dated Mar. 2, 2023 (27 pgs).
Response to Non-Final Office Action for U.S. Appl. No. 17/864,702, filed Jun. 2, 2023 (12 pgs.).
Final Office Action in U.S. Appl. No. 17/864,702, dated Oct. 2, 2023 (15 pgs).
Response to Final Office Action for U.S. Appl. No. 17/864,702, filed Dec. 21, 2023 (7 pgs.).

* cited by examiner

METHODS OF TREATING PARKINSON'S DISEASE AND/OR LEWY BODY DISEASE OR DISORDER(S)

CROSS-REFERENCE TO RELATED APPLICATIONS

This application claims the benefit of priority under 35 U.S.C. §§ 119 and 365 of International Application No. PCT/US2021/042974, filed Jul. 23, 2021, which is incorporated by reference herein in its entirety for any purpose.

FIELD

The present disclosure relates to methods of treating Parkinson's Disease and/or Lewy body disease or disorder(s), including Parkinson's disease dementia and dementia with Lewy bodies.

BACKGROUND

Parkinson's disease (PD) is a common neurodegenerative disease characterized by a movement disorder consisting of bradykinesia, rest tremor, and rigidity, along with postural instability, a range of other more-subtle motor features, and many non-motor features (Kalia, 2015). The clinical diagnosis of PD follows validated criteria (Postuma, 2015). Globally, PD prevalence ranges from 1 to 2 per 1000, and is increasing with age; 1% of the population over 60 years suffers from PD (Tysnes, 2017). The prevalence of PD has more than doubled between 1990 and 2016 (Rocca, 2018). There is a significant correlation between quality of life scores and non-motor symptoms (Duncan, 2014). The point prevalence of PD dementia (PDD) is close to 30% and the incidence rate is increased 4 to 6 times as compared to controls. The cumulative prevalence is very high; at least 75% of PD patients who survive for more than 10 years will develop dementia. In addition, mild cognitive impairment (MCI) is common even at disease onset, and is associated with a shorter time to dementia (Aarsland, 2010a; Helv, 2008). At presentation, 25% of individuals with PD exhibit mild cognitive impairment (Aarsland, 2010b) PD, PDD, and dementia with Lewy bodies (DLB) have been grouped under an umbrella term referred to as Lewy body disorders (Lippa, 2007). DLB is characterized by Lewy body pathology at autopsy, which is also seen in PD and PDD; however, there are no definite pathological criteria that separate DLB, PD, and PDD from each other. In general, DLB and PDD are clinically distinguished by the sequence of their symptoms. If dementia occurs before, concurrently, or within 1 year of motor parkinsonism, DLB is diagnosed; if dementia occurs more than 1 year after an established PD diagnosis, then PDD is diagnosed (Emre, 2007).

PDD is a progressive disorder, with considerable variability from patient to patient. Virtually every individual with PD experiences some degree of cognitive deficit, ranging from mild cognitive impairment to dementia. Patients diagnosed with PDD have a substantially reduced life expectancy compared to persons in the general population (Buter, 2008).

Growing evidence suggests that complex central nervous system (CNS) disorders, like PDD, are unlikely to be caused by a single route of pathology; they are likely the result of a multifactorial interplay related to genetics, age, and environment. Pharmacological stimulation of a critical neurotrophic factor system (HGF/MET) may stop neurodegeneration and promote neuro-regeneration. Neurotrophic factors represent a promising therapeutic target for the treatment of dementia caused by neurodegeneration, including PDD, by protecting existing neurons, promoting synaptogenesis, stimulating neuronal growth, and inducing regenerative mechanisms. Pharmacological stimulation of neurotrophic systems has the potential to treat all stages of PDD by directly targeting neurodegeneration, improving cognition, and addressing multiple aspects of the disease, by decreasing inflammation and improving cerebral blood flow (Funakoshi, 2011). The therapeutic promise of neurotrophic factors in neurodegenerative disorders is hampered by the lack of efficient and non-invasive delivery to the brain. Gene therapy strategies, primarily using adeno-associated viral vectors, have been developed and clinically evaluated for therapeutic potential in PDD patients. These strategies are largely hindered by challenges related to gene delivery and transduction with limited brain exposure, uncontrollable dose over long-term treatment, and potential immune complications (Piguet, 2017).

Therefore, a small molecule approach capable of passing the blood brain barrier and entering all regions of the brain, presents a superior therapeutic strategy for targeting neurotrophic factors to treat neurodegenerative disorders.

SUMMARY

The present invention provides, in some embodiments, methods of treating Parkinson's disease dementia.

Embodiment 1. A method of treating Parkinson's disease (PD) and/or Lewy body disease or disorder(s) (LBD), comprising administering to a patient in need thereof 2-90 mg per day of a compound of formula A19

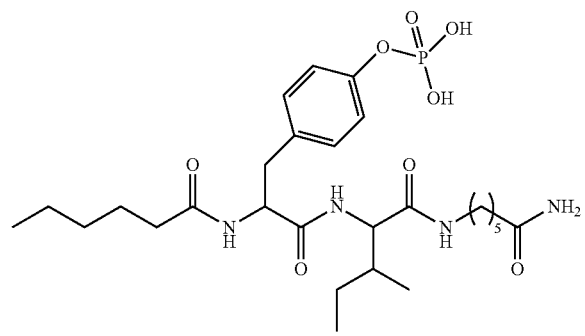

A19 or a pharmaceutically acceptable salt thereof.

Embodiment 2. A method of treating Parkinson's Disease Dementia (PDD), comprising administering to a patient in need thereof 2-90 mg per day of a compound of formula A19

A19

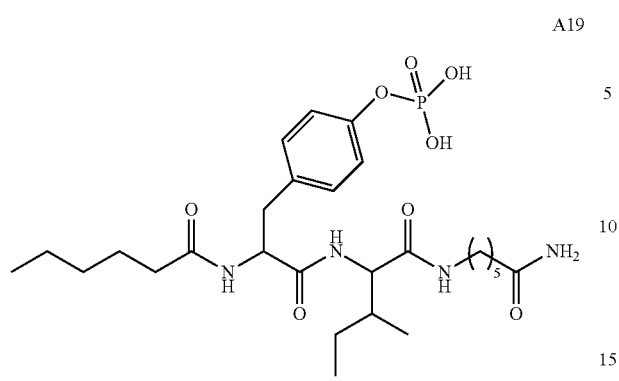

or a pharmaceutically acceptable salt thereof.

Embodiment 3. A method of treating dementia with Lewy bodies (DLB), comprising administering to a patient in need thereof 2-90 mg per day of a compound of formula A19

A19

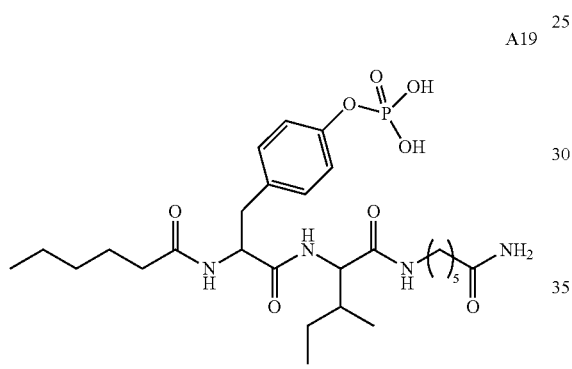

or a pharmaceutically acceptable salt thereof.

Embodiment 4. A method of treating mild to moderate dementia associated with Parkinson's disease (PD), comprising administering to a patient in need thereof 2-90 mg per day of a compound of formula A19

A19

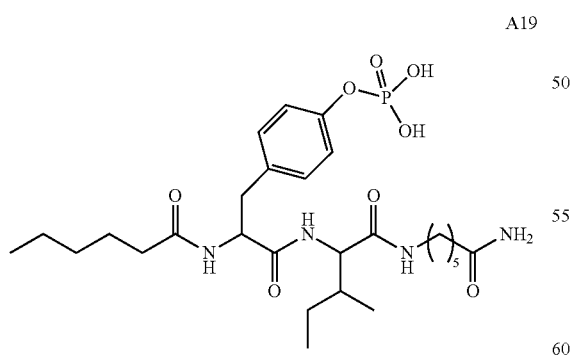

or a pharmaceutically acceptable salt thereof.

Embodiment 5. A method of improving event related potential (ERP) P300 latency in a patient diagnosed with PDD and/or DLB, comprising administering to the patient thereof 2-90 mg per day of a compound of formula A19

A19

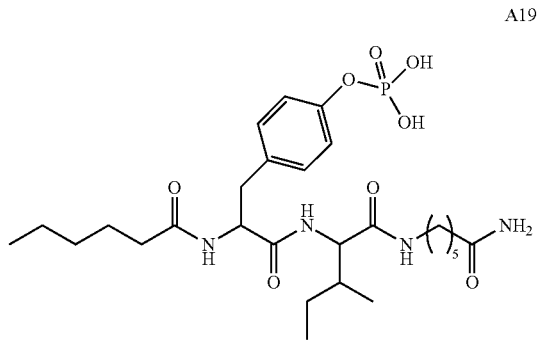

or a pharmaceutically acceptable salt thereof.

Embodiment 6. A method of slowing the decline in cognition or improving cognition in a patient diagnosed with PDD and/or DLB, comprising administering to the patient 2-90 mg per day of a compound of formula A19

A19

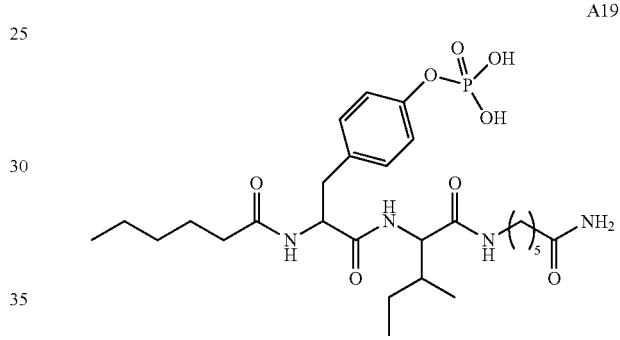

or a pharmaceutically acceptable salt thereof.

Embodiment 7. A method of slowing the decline in the ability to perform activities of daily living and verbal fluency or improving the ability to perform activities of daily living and verbal fluency in a patient diagnosed with PDD and/or DLB, comprising administering to the patient 2-90 mg per day of a compound of formula A19

A19

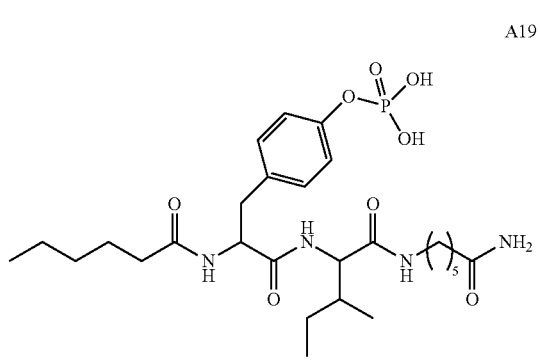

or a pharmaceutically acceptable salt thereof.

Embodiment 8. A method of slowing the decline in functional or cognitive capacity in a patient diagnosed with PDD and/or DLB, comprising administering to the patient 2-90 mg per day of a compound of formula A19

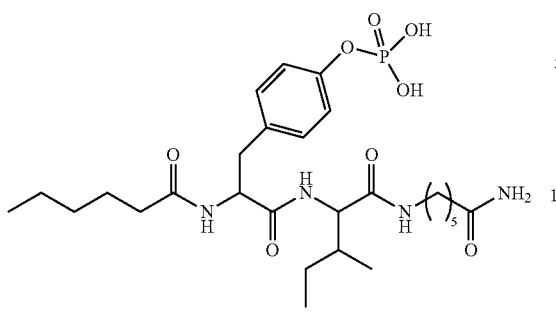

or a pharmaceutically acceptable salt thereof.

Embodiment 9. A method of slowing clinical decline in a patient diagnosed with PDD and/or DLB, comprising administering to the patient 2-90 mg per day of a compound of formula A19

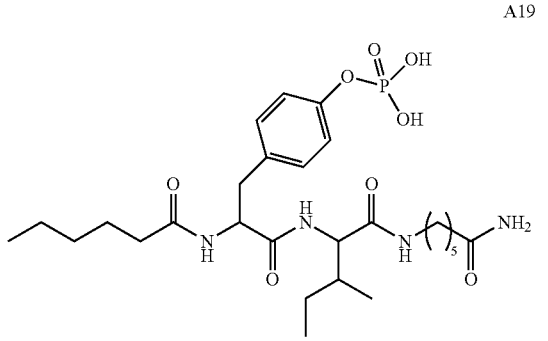

or a pharmaceutically acceptable salt thereof.

Embodiment 10. A method of improving executive memory function in a patient diagnosed with PDD and/or DLB, comprising administering to the patient 2-90 mg per day of a compound of formula A19

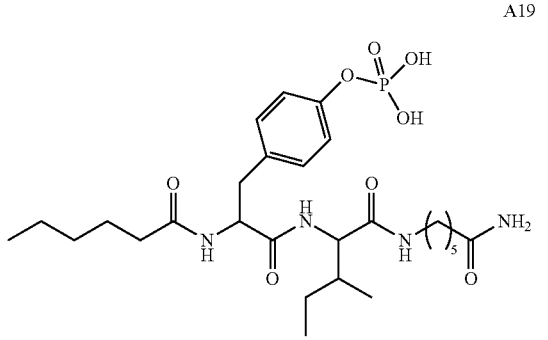

or a pharmaceutically acceptable salt thereof.

Embodiment 11. The method of any one of the preceding embodiments, comprising treating dementia.

Embodiment 12. The method of any one of the preceding embodiments, wherein the treating comprises improving one or more symptoms of dementia.

Embodiment 13. The method of any one of the preceding embodiments, wherein the treating comprises improving one or more symptoms of a motor disorder.

Embodiment 14. The method of any one of the preceding embodiments, wherein the patient has been diagnosed with PDD.

Embodiment 15. The method of any one of the preceding embodiments, wherein the patient has been diagnosed with Lewy body disease or disorder(s) (LBD).

Embodiment 16. The method of any one of the preceding embodiments, wherein the patient has been diagnosed with probable idiopathic Parkinson's disease or probable Lewy body disease or disorder(s) (LBD).

Embodiment 17. The method of any one of the preceding embodiments, wherein the patient has been diagnosed with probable idiopathic Parkinson's disease or probable LBD for at least one year.

Embodiment 18. The method of any one of the preceding embodiments, wherein the patient has been diagnosed with Parkinson's disease.

Embodiment 19. The method of any one of the preceding embodiments, wherein the patient has been diagnosed with PD for at least one year.

Embodiment 20. The method of any one of the preceding embodiments, wherein the patient has been diagnosed with PDD inclusive of probable LBD.

Embodiment 21. The method of any one of the preceding embodiments, wherein the patient has a MOCA score between 11 and 23, between 12 and 23, between 13 and 23, between 14 and 23, between 15 and 23, between 16 and 23, between 17 and 23, between 18 and 23, between 19 and 23, between 20 and 23, between 21 and 23, between 22 and 23, between 11 and 22, between 11 and 21, between 11 and 20, between 11 and 19, between 11 and 18, between 11 and 17, between 11 and 16, between 11 and 15, between 11 and 14, between 11 and 13, between 11 and 12, prior to the start of treatment with the compound of formula A19.

Embodiment 22. The method of any one of the preceding embodiments, wherein the patient is concurrently treated with an acetylcholinesterase inhibitor (AChEI) other than high dose donepezil.

Embodiment 23. The method of any one of the preceding embodiments, wherein the patient is between age 40 and 85.

Embodiment 24. The method of any one of the preceding embodiments, wherein the patient is at Hoehn-Yahr stage 1 to 4.

Embodiment 25. The method of any one of the preceding embodiments, wherein the patient is at Hoehn-Yahr stage 2 or Hoehn-Yahr stage 3.

Embodiment 26. The method of any one of the preceding embodiments, wherein the compound of formula A19 or the pharmaceutically acceptable salt thereof is administered by subcutaneous injection.

Embodiment 27. The method of any one of the preceding embodiments, comprising administering the compound of formula A19 or the pharmaceutically acceptable salt thereof at a dose of 2 mg, 10 mg, 20 mg, 30 mg, 40 mg, 50 mg, 60 mg, 70 mg, 80 mg, or 90 mg.

Embodiment 28. The method of any one of the preceding embodiments, comprising administering the compound of formula A19 or the pharmaceutically acceptable salt thereof at a dose of 40 mg or 70 mg.

Embodiment 29. The method of any one of the preceding embodiments, comprising administering the compound of formula A19 or the pharmaceutically acceptable salt thereof at a dose of 40 mg.

Embodiment 30. The method of any one of the preceding embodiments, comprising administering the compound of formula A19 or the pharmaceutically acceptable salt thereof at a dose of 70 mg.

Embodiment 31. The method of any one of the preceding embodiments, comprising administering the compound of formula A19 or the pharmaceutically acceptable salt thereof for 26 weeks or more.

Embodiment 32. The method of any one of the preceding embodiments, which slows the decline in functional or cognitive capacity in the patient.

Embodiment 33. The method of any one of the preceding embodiments, which slows the decline in cognition in the patient.

Embodiment 34. The method of any one of the preceding embodiments, which improves cognition in the patient.

Embodiment 35. The method of any one of the preceding embodiments, which slows the decline in the ability to perform activities of daily living and verbal fluency in the patient.

Embodiment 36. The method of any one of the preceding embodiments, which improves the ability to perform activities of daily living and verbal fluency in the patient.

Embodiment 37. The method of any one of embodiments 32 to 36, wherein the slowing of the decline or the improvement is determined after administering the treatment for at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks.

Embodiment 38. The method of any one of the preceding embodiments, wherein cognitive capacity is assessed by determining the patient's score before and after administration of the compound of formula A19 or the pharmaceutically acceptable salt thereof using a 13-item Alzheimer's Disease Assessment Scale—cognitive subscale (ADAS-Cog13).

Embodiment 39. The method of embodiment 38, wherein cognitive capacity is assessed prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 40. The method of any one of the preceding embodiments, which reduces the rate of decline, stabilizes, or improves ADAS-Cog13.

Embodiment 41. The method of embodiment 40, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 42. The method of any one of embodiments 38 to 41, wherein the onset of the effect on ADAS-Cog13 begins by 2 weeks, or by 4 weeks, or by 6 weeks, or by 8 weeks, or by 10 weeks, or by 12 weeks, or by 14 weeks, or by 16 weeks, or by 18 weeks, or by 20 weeks, or by 22 weeks, or by 24 weeks, or by 26 weeks after the start of treatment.

Embodiment 43. The method of any one of embodiments 38 to 42, wherein the effect on ADAS-Cog13 is maintained for at least 2 weeks or at least 4 weeks after the end of treatment.

Embodiment 44. The method of any one of the preceding embodiments, which reduces the rate of decline, stabilizes, or improves a Clinician Global Impression of Change (CGI-C) score.

Embodiment 45. The method of embodiment 44, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 46. The method of embodiment 44 or embodiment 45, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 47. The method of any one of the preceding embodiments, which reduces the rate of decline, stabilizes, or improves a Clinician Global Impression of Severity (CGI-S) score.

Embodiment 48. The method of embodiment 47, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 49. The method of embodiment 47 or embodiment 48, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 50. The method of any one of the preceding embodiments, which reduces the rate of decline, stabilizes, or improves an Alzheimer's disease cooperative study-activities of daily living, 23-item version (ADCS-ADL23) score.

Embodiment 51. The method of embodiment 50, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 52. The method of embodiment 50 or embodiment 51, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 53. The method of any one of the preceding embodiments, which reduces the rate of decline, stabilizes, or improves a Movement Disorder Society-Unified Parkinson's Disease Rating Scale (MDS-UPDRS) score.

Embodiment 54. The method of any one of the preceding embodiments, which reduces the rate of decline, stabilizes, or improves a MDS-UPDRS, Part I score.

Embodiment 55. The method of any one of the preceding embodiments, which reduces the rate of decline, stabilizes, or improves a MDS-UPDRS, Part I, domains 1.2, 1.5, and/or 1.8 score.

Embodiment 56. The method of any one of embodiments 53 to 55, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 57. The method of any one of embodiments 53 to 56, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 58. The method of any one of the preceding embodiments, which reduces the rate of decline, stabilizes, or improves a Caregiver Global Impression of Change (CaGI-C) score.

Embodiment 59. The method of embodiment 58, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 60. The method of embodiment 58 or embodiment 59, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 61. The method of any one of the preceding embodiments, which reduces the rate of decline, stabilizes, or improves a Non-Motor Symptom Scale (NMSS) score.

Embodiment 62. The method of any one of the preceding embodiments, which reduces the rate of decline, stabilizes, or improves a NMSS domain 2 and/or domain 4 score.

Embodiment 63. The method of embodiment 61 or embodiment 62, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 64. The method of any one of embodiments 61 to 63, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 65. The method of any one of the preceding embodiments, which reduces the rate of decline, stabilizes, or improves a Mini-Mental State Examination (MMSE) score.

Embodiment 66. The method of embodiment 65, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 67. The method of embodiment 65 or embodiment 66, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 68. The method of any one of the preceding embodiments, which reduces the rate of decline, stabilizes, or improves a Controlled Oral Word Association Test (COWAT) score.

Embodiment 69. The method of embodiment 68, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 70. The method of embodiment 68 or embodiment 69, wherein reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 71. The method of any one of the preceding embodiments, which provides persistence in improvement in ERP 300 latency.

Embodiment 72. The method of embodiment 71, which provides persistence in improvement in ERP 300 latency at least 30 weeks after the start of treatment.

Embodiment 73. The method of any one of the preceding embodiments, which provides fast improvement or normalization of ERP P300 values.

Embodiment 74. The method of any one of the preceding embodiments, which provides fast improvement or normalization of EPR P300 latency values.

Embodiment 75. The method of any one of the preceding embodiments, which provides fast improvement or normalization of ERP P300 latency values with some maintenance of effect at at least 26 weeks of treatment.

Embodiment 76. The method of any one of the preceding embodiments, which provides fast improvement or normalization of ERP P300 latency values, which is maintained at at least 26 weeks of treatment.

Embodiment 77. The method of any one of the preceding embodiments, which improves event-related potential (ERP) P300 latency.

Embodiment 78. The method of any one of embodiments 71 to 77, wherein the improvement or normalization occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 79. The method of any one of the preceding embodiments, which reduces the rate of decline, stabilizes, or improves a non-motor symptom in the patient.

Embodiment 80. The method of embodiment 79, wherein the non-motor symptom includes delusions, apathy, hallucinations, daytime sleepiness, and/or depression.

Embodiment 81. The method of embodiment 79 or embodiment 80, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 82. The method of any one of embodiments 79 to 81, wherein reducing the rate of decline, stabilizing, or improving is assessed by determining the patient's symptom(s) prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 83. The method of any one of the preceding embodiments, which reduces the rate of decline, stabilizes, or improves a motor symptom in the patient.

Embodiment 84. The method of embodiment 83, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 85. The method of embodiment 83 or embodiment 84, wherein reducing the rate of decline, stabilizing, or improving is assessed by determining the patient's symptom(s) prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

Embodiment 86. The method of any one of the preceding embodiments, which has an acceptable safety and tolerability profile.

Embodiment 87. The method of any one of the preceding embodiments, which is generally safe and well tolerated.

Embodiment 88. The method of any one of the preceding embodiments, which is not associated with an increase in nausea, vomiting or tremor.

Embodiment 89. The method of any one of the preceding embodiments, which does not produce drug-drug interactions with a drug administered for Parkinson's disease.

Embodiment 90. The method of any one of the preceding embodiments, which does not prolong the QT interval.

Embodiment 91. The method of any one of the preceding embodiments, comprising administering a sodium salt of the compound of formula A19.

Embodiment 92. The method of any one of the preceding embodiments, comprising administering a monosodium salt of the compound of formula A19.

Embodiment 93. The method of any one of the preceding embodiments, comprising administering ATH-1017.

Embodiment 94. The method of any one of the preceding embodiments, wherein the patient is acetylcholinesterase inhibitor (AChEI) naïve or received an AChEI in the past, or received AChEI in the past and discontinued at least 4 weeks prior to administration of the compound.

Embodiment 95. The method of any one of embodiments 1 to 22 and 23 to 94, wherein the patient is not concurrently treated with an AChEI.

DETAILED DESCRIPTION

ATH-1017 is an experimental treatment for Lewy body disease or disorder(s) (LBD), including Parkinson's disease dementia (PDD) and/or dementia with Lewy bodies (DLB), formulated as a sterile solution for subcutaneous (SC) injection. ATH-1017 is a prodrug, which is rapidly converted to the active drug ATH-1001 in the plasma after SC injection. ATH-1017 was developed as a water-soluble prodrug of ATH-1001 to allow SC dosing in aqueous vehicles. The active drug ATH-1001 acts as an agonist of the hepatocyte growth factor (HGF) receptor and its tyrosine kinase, MET in the brain. The HGF/MET system presents a new therapeutic target to treat neurodegeneration and restore cognitive, behavioral, functional and motor capacities in LBD such as PDD.

Definitions and General Parameters

As used in the present specification, the following terms and phrases are generally intended to have the meanings as set forth below, except to the extent that the context in which they are used indicates otherwise.

Abbreviations that may be used in this description:

| Abbreviation | Definition |
| --- | --- |
| AChEI | Acetylcholinesterase inhibitor |
| AD | Alzheimer's disease |
| ADAS-Cog$_{13}$ | Alzheimer's Disease Assessment Scale-Cognitive Subscale, 13-item version |
| ADCS-ADL23 | Alzheimer's disease cooperative study-activities of daily living, 23-item version |
| AE | Adverse event |
| AKT | Protein kinase B |
| ALP | Alkaline phosphatase |
| ALT | Alanine aminotransferase |
| aPTT | Activated partial thromboplastin time |
| AST | Aspartate aminotransferase |
| BMI | Body mass index |
| CaGI-C | Caregiver Global Impression of Change |
| CBC | Complete blood count |
| CBD | Cannabidiol |
| CGIC or CGI-C | Clinical Global Impression of Change |
| CGI-S | Clinical Global Impression of Severity |
| COWAT | Controlled Oral Word Association test |
| CPK | Creatine phosphokinase |
| CRO | Contract research organization |
| CYP3A4 | Cytochrome P450 3A4 |
| $C_{max}$ | Maximum concentration |
| CNS | Central nervous system |
| CPK | Creatine phosphokinase |
| C-SSRS | Columbia-suicide severity rating scale |
| CT | Computerized tomography |
| DSM-5 | Diagnostic and Statistical Manual of Mental Disorders, 5$^{th}$ Edition |
| DSMB | Data safety monitoring board |
| DLB | Dementia with Lewy bodies |
| ECG | Electrocardiogram |
| eCRF | Electronic case report form |
| EDC | Electronic data capture |
| ERP | Event-related potentials |
| ET | Early termination |
| FSH | Follicle-stimulating hormone |
| fT3 | Free tri-iodothyronine |
| fT4 | Free thyroxine |
| FWER | Family-wise error rate |
| GBA | Glucocerebrosidase |
| GCP | Good Clinical Practice |
| GDS | Geriatric depression scale |
| GGT | Gamma-glutamyl transferase |
| GLP | Good Laboratory Practice |
| GST | Global Statistical Test |
| Hb1Ac | Glycated hemoglobin |
| HBsAg | Hepatitis B surface antigen |
| HCV | Hepatitis C virus |
| HGF | Hepatocyte growth factor |

| Abbreviation | Definition |
| --- | --- |
| HIV | Human immunodeficiency virus |
| HR | Heart rate |
| ICF | Informed consent form |
| ICH | International Council for Harmonisation |
| IEC | Independent ethics committee |
| IMP | Investigational medicinal product |
| INR | International normalized ratio |
| IRB | Institutional review board |
| IRT | Interactive response technology |
| LAR | Legally authorized representative |
| LBD | Lewy body disease or disorder(s) |
| LTP | Long-term potentiation |
| MAO-B | Monoamine oxidase B |
| MAPK | Mitogen-activated protein kinase |
| MCT | Medium-chain triglyceride |
| MDS-UPDRS | Movement Disorder Society-Unified Parkinson's Disease Rating Scale |
| MET | MET receptor tyrosine kinase |
| mITT | Modified intent-to-treat |
| MMRM | Mixed model for repeated measures |
| MMSE | Mini-Mental State Examination |
| MOCA | Montreal Cognitive Assessment |
| MRI | Magnetic resonance imaging |
| NMDA | N-methyl D-aspartate |
| NMSS | Non-Motor Symptom Scale |
| OD | Once-daily |
| OLEX | Open-label extension |
| P | Phosphorylated |
| PD | Parkinson's disease |
| PDD | Parkinson's disease dementia |
| PI3K | Phosphoinositide 3-kinase |
| PK | Pharmacokinetic(s) |
| PK-PD | Pharmacokinetic-pharmacodynamic |
| PKC | Protein kinase C |
| PLCγ | Phospholipase C-gamma |
| PRN | As needed |
| PT | Prothrombin time |
| QTcF | Corrected QT interval using Fridericia's formula |
| RAC1 | Ras-related C3 botulinum toxin substrate 1 |
| RAF | Rapidly accelerated fibrosarcoma (protein) |
| RBC | Red blood cells |
| SAE | Serious adverse event |
| SAP | Statistical analysis plan |
| SBP | Systolic blood pressure |
| SC | Subcutaneous |
| PGI-S | Patient Global Impression of Severity |
| SARS-CoV-2 | Severe acute respiratory syndrome coronavirus 2 |
| SOP | Standard operating procedure |
| STAT3 | Signal transducer and activator of transcription 3 |
| THC | Tetrahydrocannabinol |
| TSH | Thyroid-stimulating hormone |
| ULN | Upper limit of normal |
| US(A) | United States (of America) |
| VAS | Visual analog scale |
| WBC | White blood cells |

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

In some embodiments, the compounds of the present disclosure can be in the form of a "prodrug." The term "prodrug" is defined in the pharmaceutical field as a biologically inactive derivative of a drug that upon administration to the human body is converted to the biologically active parent drug according to some chemical or enzymatic pathway. Examples of prodrugs include esterified carboxylic acids.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine, amino acids, or other bases known to persons skilled in the art. The compounds of the present disclosure which contain one or more basic groups, i.e., groups which can be protonated, can be present and can be used according to the disclosure in the form of their addition salts with inorganic or organic acids.

The present disclosure provides pharmaceutical compositions comprising a compound of the present disclosure, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure can encompass any composition made by admixing at least one compound of the present disclosure and a pharmaceutically acceptable carrier.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's *Pharmaceutical Sciences*, Mace Publishing Co., Philadelphia, Pennsylvania 17th Ed. (1985); and *Modern Pharmaceutics*, Marcel Dekker, Inc. 3rd Ed. (G. S. Banker & C. T. Rhodes, Eds.).

The terms "therapeutically effective amount" and "effective amount" are used interchangeably and refer to an amount of a compound that is sufficient to effect treatment as defined herein, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver.

The term "treatment" or "treating" means administering a compound or pharmaceutically acceptable salt thereof for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

ATH-1017 and Related Compounds

ATH-1017 is a pharmaceutically acceptable salt of the compound having the formula of A19:

A19

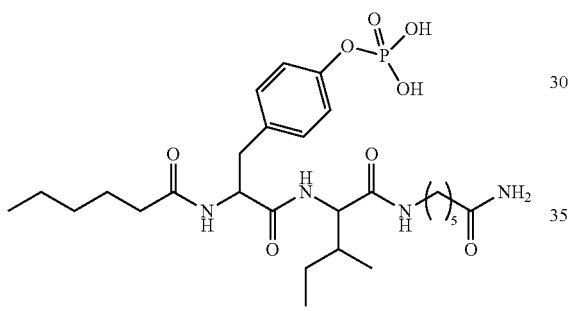

As used herein, and in the absence of a specific reference to a particular pharmaceutically acceptable salt and/or solvate of ATH-1017, any dosages, whether expressed in e.g. milligrams or as a % by weight, should be taken as referring to the amount of ATH-1017, i.e. the amount of:

A19

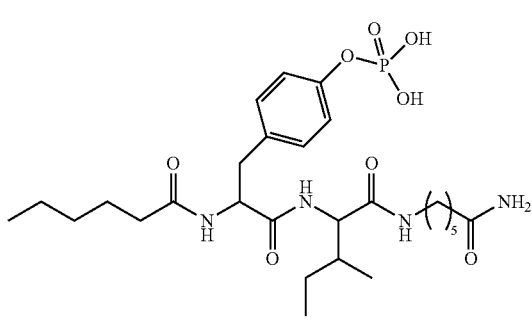

For example, therefore, a reference to "40 mg ATH-1017 or a pharmaceutically acceptable salt and/or solvate thereof" means an amount of ATH-1017 or a pharmaceutically acceptable salt and/or solvate thereof which provides the same amount of ATH-1017 as 40 mg of A19 free acid.

Nonlimiting exemplary pharmaceutically acceptable salts of A19 include:

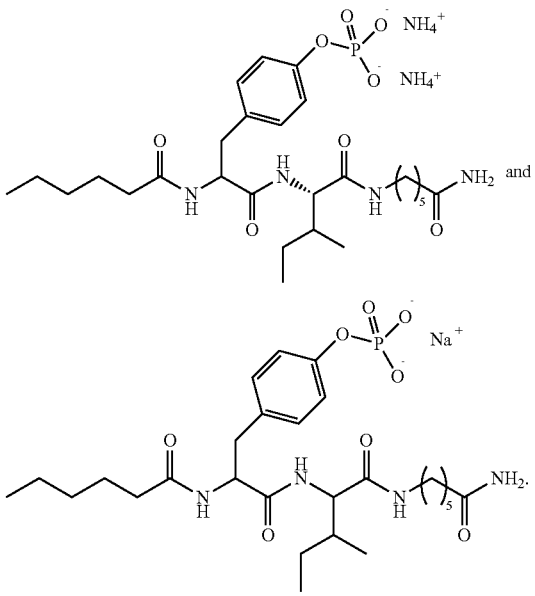

Unless otherwise indicated, ATH-1017 refers to the monosodium salt of A19, shown below:

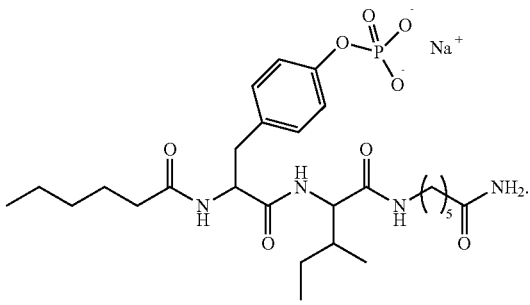

The compound of A19, and pharmaceutically acceptable salts thereof, including ATH-1017, may be synthesized and characterized using methods known to those of skill in the art, such as those described in PCT Publication No. WO 2017/210489 A1.

In some embodiments, ATH-1017 is formulated for subcutaneous administration. In some such embodiments, ATH-1017 is provided in a pre-filled syringe containing 1 mL of 40 mg/mL ATH-1017 or 70 mg/mL ATH-1017. In some embodiments, the ATH-1017 is in a solution comprising 10 mM sodium phosphate.

Methods of Treating Parkinson's Disease and/or Lewy Body Disease or Disorder(s)

Provided herein are methods of treating Parkinson's Disease (PD) and/or Lewy body disease or disorder(s) (LBD), including Parkinson's Disease Dementia (PDD) and/or dementia with Lewy bodies (DLB), comprising administering to a patient a therapeutically effective amount of ATH-1017.

In some embodiments, a method of treating Parkinson's disease (PD) and/or Lewy body disease or disorder(s) (LBD) is provided, comprising administering to a patient in need thereof 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, a method of treating Parkinson's Disease Dementia (PDD) is provided, comprising administering to a patient in need thereof 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, a method of treating dementia with Lewy bodies (DLB) is provided, comprising administering to a patient in need thereof 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, a method of treating mild to moderate dementia associated with Parkinson's disease (PD) is provided, comprising administering to a patient in need thereof 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, a method of improving event related potential (ERP) P300 latency in a patient diagnosed with PDD and/or DLB is provided, comprising administering to the patient 2-90 mg per day of a compound of formula A19 or a pharmaceutically acceptable salt thereof, such as a sodium salt of the compound of formula A19, such as a monosodium salt of the compound of formula A19, such as ATH-1017.

Event-related potential (ERP) P300 latency is a functional measure of working memory processing speed and executive function that highly correlates with cognition. In some embodiments, administration of ATH-1017 in PDD and/or DLB subjects significantly improves P300 latency.

In some embodiments, a method of slowing the decline in cognition or improving cognition in a patient diagnosed with PDD and/or DLB is provided, comprising administering to the patient 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, a method of slowing the decline in the ability to perform activities of daily living and verbal fluency or improving the ability to perform activities of daily living and verbal fluency in a patient diagnosed with PDD and/or DLB is provided, comprising administering to the patient 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, a method of slowing the decline in functional or cognitive capacity in a patient diagnosed with PDD and/or DLB is provided, comprising administering to the patient 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, a method of slowing clinical decline in a patient diagnosed with PDD and/or DLB is provided, comprising administering to the patient 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, a method of improving executive memory function in a patient diagnosed with PDD and/or DLB is provided, comprising administering to the patient 2-90 mg per day of a compound of formula A19 or a pharmaceutically acceptable salt thereof, such as a sodium salt of the compound of formula A19, such as a monosodium salt of the compound of formula A19, such as ATH-1017.

In some embodiments, the method comprises treating dementia. In some embodiments, the method comprises improving one or more symptoms of dementia. In some embodiments, the method comprises improving one or more symptoms of a motor disorder.

In some embodiments, the patient has been diagnosed with PDD.

In some embodiments, the patient has been diagnosed with LBD.

In some embodiments, the patient has been diagnosed with probable idiopathic Parkinson's disease or probable Lewy body disease or disorder(s) (LBD). In some embodiments, the patient has been diagnosed with probable idiopathic Parkinson's disease or probable LBD for at least one year.

In some embodiments, the patient has been diagnosed with Parkinson's disease. In some embodiments, the patient has been diagnosed with PD for at least one year.

In some embodiments, the patient has been diagnosed with PDD inclusive of probable LBD.

In some embodiments, the patient has a Montreal Cognitive Assessment (MOCA) score between 11 and 23, between 12 and 23, between 13 and 23, between 14 and 23, between 15 and 23, between 16 and 23, between 17 and 23, between 18 and 23, between 19 and 23, between 20 and 23, between 21 and 23, between 22 and 23, between 11 and 22, between 11 and 21, between 11 and 20, between 11 and 19, between 11 and 18, between 11 and 17, between 11 and 16, between 11 and 15, between 11 and 14, between 11 and 13, between 11 and 12, prior to the start of treatment with the compound of formula A19.

In some embodiments, the patient is concurrently treated with an acetylcholinesterase inhibitor (AChEI) other than high dose donepezil. In some embodiments, the patient is not being concurrently treated with an AChEI.

In some embodiments, the patient is acetylcholinesterase inhibitor (AChEI) naïve. In some embodiments, the patient received an AChEI in the past. In some embodiments, the patient discontinued AChEI therapy at least 4 weeks prior to administration of the compound of formula A19.

In some embodiments, the patient is between age 40 and 85.

In some embodiments, the patient is at Hoehn-Yahr stage 1 to 4. In some embodiments, the patient is at Hoehn-Yahr stage 2 or Hoehn-Yahr stage 3.

In some embodiments, the compound of formula A19 or the pharmaceutically acceptable salt thereof, such as a sodium salt of the compound of formula A19, such as a monosodium salt of the compound of formula A19, such as ATH-1017, is administered by subcutaneous injection.

In some embodiments, the compound of formula A19 or the pharmaceutically acceptable salt thereof is administered at a dose of 2 mg, 10 mg, 20 mg, 30 mg, 40 mg, 50 mg, 60 mg, 70 mg, 80 mg, or 90 mg. In some embodiments, the compound of formula A19 or the pharmaceutically acceptable salt thereof is administered at a dose of 40 mg or 70 mg.

In some embodiments, the compound of formula A19 or the pharmaceutically acceptable salt thereof, such as a sodium salt of the compound of formula A19, such as a monosodium salt of the compound of formula A19, such as ATH-1017, is administered at a dose of 40 mg. In some embodiments, the compound of formula A19 or the pharmaceutically acceptable salt thereof, such as a sodium salt of the compound of formula A19, such as a monosodium salt of the compound of formula A19, such as ATH-1017, is administered at a dose of 70 mg.

In some embodiments, the compound of formula A19 or the pharmaceutically acceptable salt thereof, such as a sodium salt of the compound of formula A19, such as a monosodium salt of the compound of formula A19, such as ATH-1017, is administered for 26 weeks or more.

In some embodiments, the methods of treatment described herein slow the decline in or improve functional or cognitive capacity in the patient. In some embodiments, the methods of treatment slow the decline in or improve cognition in the patient. In some embodiments, the methods of treatment slow the decline in or improve the ability to perform activities of daily living and verbal fluency in the patient.

In some embodiments, the methods of treatment described herein improve cognition in the patient. In some embodiments, the methods of treatment improve the ability to perform activities of daily living and verbal fluency in the patient.

In some embodiments, the slowing of the decline or the improvement is determined after administering the treatment for at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks.

Various methods are useful in assessing the cognitive capacity of the patient.

In some embodiments, cognitive capacity is assessed by determining the patient's score before and after administration of the compound of formula A19 or the pharmaceutically acceptable salt thereof using a 13-item Alzheimer's Disease Assessment Scale—cognitive subscale (ADAS-Cog13). In some embodiments, cognitive capacity is assessed prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, the method of treatment reduces the rate of decline, stabilizes, or improves ADAS-Cog13. In some embodiments, the onset of the effect on ADAS-Cog13 begins by 2 weeks, or by 4 weeks, or by 6 weeks, or by 8 weeks, or by 10 weeks, or by 12 weeks, or by 14 weeks, or by 16 weeks, or by 18 weeks, or by 20 weeks, or by 22 weeks, or by 24 weeks, or by 26 weeks after the start of treatment. In some embodiments, the effect on ADAS-Cog13 is maintained for at least 2 weeks or at least 4 weeks after the end of treatment.

In some embodiments, the method of treatment reduces the rate of decline, stabilizes, or improves a Clinician Global Impression of Change (CGI-C) score. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves a Clinician Global Impression of Severity (CGI-S) score. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves an Alzheimer's disease cooperative study-activities of daily living, 23-item version (ADCS-ADL23) score. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves a Movement Disorder Society-Unified Parkinson's Disease Rating Scale (MDS-UPDRS) score, such as a MDS-UPDRS, Part I score, such as a MDS-UPDRS, Part I, domains 1.2, 1.5, and/or 1.8 score. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves a Caregiver Global Impression of Change (CaGI-C) score. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves a Non-Motor Symptom Scale (NMSS) score, such as a NMSS domain 2 and/or domain 4 score. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves a Mini-Mental State Examination (MMSE) score. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves a Controlled Oral Word Association Test (COWAT) score. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment provides persistence in improvement in ERP 300 latency, such as at least 30 weeks after the start of treatment. In some embodiments, the method of treatment provides fast improvement or normalization of ERP P300 values, such as fast improvement or normalization of EPR P300 latency value, such as fast improvement or normalization of ERP P300 latency values with some maintenance of effect at at least 26 weeks of treatment, such as fast improvement or normalization of ERP P300 latency values, which is maintained at at least 26 weeks of treatment.

In some embodiments, the method of treatment improves event-related potential (ERP) P300 latency. In some embodiments, the method of treatment provides improvement or normalization of ERP P300 latency values by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves a non-motor symptom in the patient, such as delusions, apathy, hallucinations, daytime sleepiness, and/or depression. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment reduces the rate of decline, stabilizes, or improves a motor symptom in the patient. In some embodiments, the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment. In some embodiments, reducing the rate of decline, stabilizing, or improving is assessed by determining the patient's score prior to the start of treatment and at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

In some embodiments, the method of treatment has an acceptable safety and tolerability profile. In some embodiments, the method of treatment is generally safe and well tolerated.

Pharmaceutical Compositions

In some embodiments, the method includes administering ATH-1017 by subcutaneous injection.

Pharmaceutical compositions for the drugs provided herein may be in a form suitable for the administration routes. The formulations can conveniently be presented in unit dosage form and may be prepared by any of the methods well known in the art of pharmacy. Techniques and formulations generally are found in Remington's Pharmaceutical Sciences (Mack Publishing Co., Easton, Pennsylvania).

The pharmaceutical compositions of the disclosure may be in the form of a sterile injectable preparation, such as, for example, a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic monoor diglycerides. In addition, fatty acids such as, for example, oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations can be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The amount of active ingredient that may be combined with the carrier material to produce a single dosage form will vary depending upon the host treated and the particular mode of administration, such as subcutaneous injection. The pharmaceutical composition can be prepared to provide easily measurable amounts for administration. For example, in some embodiments, ATH-1017 is formulated for subcutaneous administration, provided in a pre-filled syringe containing 1 mL of 40 mg/mL ATH-1017 or 70 mg/mL ATH-1017. In some embodiments, the ATH-1017 is in a solution comprising 10 mM sodium phosphate.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that these examples are exemplary and not exhaustive. Many changes can be made in the specific embodiments which are disclosed and still obtain a like or similar result without departing from the spirit and scope of the disclosure.

Example 1: Clinical Study Evaluating ATH-1017 in Subjects with Parkinson's Disease Dementia A. Overview of Study Design In clinical studies of ATH-1017, single SC administration of 2, 6, 20, 40, 60, and 90 mg in healthy young subjects, and multiple administration of 20, 40, 60, and 80 mg (SC, OD, over 9 consecutive days) in healthy elderly subjects, and 40 mg (SC, OD, over 9 consecutive days) in AD subjects were safe and well tolerated. Injection site reactions included pain, pruritus, or erythema, were mild in nature, and resolved without specific therapy. A potential risk for hepatotoxicity identified in nonclinical studies has not been observed in human studies but will be closely monitored in this study. To date, no CNS-specific adverse events have been observed in humans.

This is a Phase 2 multicenter, randomized, double-blind, placebo-controlled, parallel-group, dose-ranging study comparing ATH-1017 40 mg/day and ATH-1017 70 mg/day with placebo in subjects with a clinical diagnosis of PDD inclusive of probable dementia with Lewy bodies (DLB) (Postuma, 2015; Emre, 2007; McKeith, 2017) and with a Montreal Cognitive Assessment (MOCA) score of 11 to 23 at Screening. The study is conducted at a total of approximately 15 centers in the USA and optionally Canada. Subjects and their caregivers are required to sign an informed consent form (ICF) and are evaluated against the inclusion/exclusion criteria during a screening period; all eligible subjects will have the option to be tested for glucocerebrosidase (GBA) genotype. Subjects who meet all inclusion/exclusion criteria will undergo baseline ERP P300 assessments at 2 separate baseline visits. At the first baseline assessment (Visit 2a, Pre-baseline, Day—10 to Day—3), ERP P300 is uploaded for quality check immediately after completion of the visit. At the second baseline visit (Visit 2b, Baseline, Day 1), no more than 10 days after the Pre-baseline visit, eligible subjects are randomized in a ratio of 1:1:1 to 1 of 3 parallel arms, either to ATH-1017 40 mg/day or ATH-1017 70 mg/day or placebo. At this Baseline visit (Visit 2b), subjects undergo pre-dose baseline and post-dose ERP P300.

Study drug is administered by subcutaneous (SC) injection once-daily (OD) preferably during daytime; subjects must not take another dose within 8 hours of the preceding dose. The first SC injection of study drug is performed on site under supervision. The subject should withhold study drug administration on the day of subsequent clinic visits; study drug administration is done on site under supervision of site staff at these visits. Each subject is required to have a primary caregiver willing to accept responsibility for supervising or, if required, administering study drug, and assessing the condition of the subject throughout the study in accordance with all protocol requirements. During the double-blind treatment period, clinic visits take place on Day 1 and thereafter at Weeks 2, 6, 12, 16, 20, and 26, with a safety follow-up visit scheduled 4 weeks after completion of the double-blind period at Week 30. On Day 1, after completion of the first dose, subjects remain on-site 2 hours for post-treatment clinical observation. ADAS-Cogn, M1VISE, and COWAT assessments occur at clinic visits in the morning at approximately the same time they were performed during the initial baseline assessment (Visit 2b). Subjects undergo post-baseline ERP P300 at clinic visits (pre- and/or post-dose timepoints).

Subjects may live at home, in a senior residential setting, or an institutional setting without the need for continuous nursing care, and should not be likely to experience a change in living conditions (e.g., institutionalization, moving to a different city, etc.), or change in primary caregiver, during participation in the trial period. The end of the study is defined as the date of the safety follow-up visit, Visit 9/Week 30. Subjects who terminate prior to Visit 8 are to complete the same assessments as Visit 8/early termination (ET).

An independent Data Safety Monitoring Board conducts periodic review and assessments of unblinded safety data (AEs, laboratory assessments, ECG, etc.) throughout the study to ensure the safety of study subjects.

Blood draws take place at scheduled clinic visits for analysis of plasma concentrations of ATH-1017 (prodrug) and ATH-1001 (active drug).

B. Subject Population

The study randomizes up to approximately 75 subjects in a 1:1:1 ratio to ATH-1017 40 mg, ATH-1017 70 mg, and placebo groups.

Inclusion Criteria

Subjects must meet all of the following inclusion criteria to participate in the study.
1) Age 40 to 85 years, inclusive at the time of signing the informed consent.
2) Subjects with a confirmed diagnosis of probable idiopathic Parkinson's disease (Postuma, 2015) or probable DLB (McKeith, 2017) for at least 1 year.
3) Dementia (PDD) diagnosed according to Emre, 2007, inclusive of probable DLB (McKeith, 2017), reported and preferably documented by subject medical records; caregiver reports with examples are acceptable.
4) MOCA score 11 to 23 inclusive at the Screening visit.
5) Body mass index (BMI) of between >16.0 and <35.0 kg/m' for females and between >18.0 and <35.0 kg/m' for males at Screening. Subjects with BMI outside the allowed BMI range but >16 and <37 kg/m$^2$ may enroll only with prior agreement of the Sponsor.
6) Female subjects of child-bearing potential must not be pregnant (i.e., a negative urine pregnancy result is required prior to randomization) and must not be breast-feeding.
7) Male and female subjects of child-bearing potential and their partners must agree to use a double-barrier method of contraception during the study, including the follow-up period, unless the partner is not of childbearing potential. Female subjects of non-childbearing potential (i.e., permanently sterilized, postmenopausal) are eligible for participation.
8) Reliable and capable support person/caregiver, who is willing to accept responsibility for supervising the treatment or, if required, administering study drug, and assessing the condition of the subject throughout the study in accordance with all protocol requirements. The support person/caregiver must see the subject at least once-daily for dose administration and/or observation.
9) Subject capable of giving signed informed consent, which includes compliance with the requirements and restrictions listed in the ICF and in this protocol. If the subject is incapable of giving informed consent in the judgment of the investigator then consent may be provided by a legally acceptable representative.
10) Written informed consent from a) subject or legally acceptable representative and b) caregiver/support person has been obtained prior to any study-related procedures, including prior to initiating screening procedures to evaluate eligibility for the study.
11) Written documentation has been obtained in accordance with the relevant country and local privacy requirements, where applicable (e.g., Written Authorization for Use and Release of Health and Research Study Information).
12) Subjects and caregivers/support persons are able, as assessed by the investigator, and willing to follow study instructions and likely to complete all required study visits.
13) Subjects must be in generally good health as assessed by the investigator from medical history and physical/neurological examination, vital signs, ECG, and standard laboratory tests.

Exclusion Criteria

Subjects who meet any of the following criteria are excluded from the study:
1) Subjects at modified Hoehn-Yahr stage 5.
2) History of significant neurologic disease, other than PDD or LBD that may affect cognition, or concurrent with the onset of dementia.
3) Subject has had neurosurgical procedure for treatment of PD, or if such procedure is anticipated or planned during the study period.
4) History of brain magnetic resonance imaging (MM) scan indicative of any other significant abnormality, which would explain a dementing process other than PDD or DLB. Note: a new MM scan is required if not done since the initial diagnosis of PD; a repeat MRI scan is required if there have been intervening changes to the subject's clinical presentation in the past 12 months. CT scan is acceptable for subjects fitted with a non-MM-safe cardiac pacemaker, or other relevant medical reason, with Medical Monitor approval.
5) History of unexplained loss of consciousness, or epileptic fits (unless febrile).
6) Inability to hear or differentiate the 2 different tones used for auditory ERP P300 assessment, as tested by the provided equipment; subjects who wear a hearing aid must remove their hearing aid during the auditory test.
7) Diagnosis with current symptoms of severe major depressive disorder (GDS score [15-item scale]>7 at Screening). In discussion with the Medical Monitor, subjects with a GDS score between 8 and 10 inclusive can be considered for study participation if the increased score is driven by specific domains related to the pandemic and its restrictions, rather than by major depression.
8) Significant suicide risk as defined by suicidal ideation based on the C-SSRS within the last 12 months, at Screening and on Day 1 (i.e., a 'yes' response to Question 4 or 5, or any specific behaviors).
9) Significant psychosis (according to the Diagnostic and Statistical Manual of Mental Disorders, [5th edition; DSM-5; American Psychiatric Association, 2013]) interfering with the ability of the subject to complete study procedures in the judgement of the investigator, for reasons such as requirement to reduce previously stable dopaminergic therapy.
10) Moderate or severe substance abuse disorder (according to DSM-5; American Psychiatric Association, 2013).
11) Untreated conditions, including hypothyroidism, diabetes mellitus, hypo- or hypertension, if clinically relevant in the judgment of the investigator. If treated, must be stably treated and symptom-free for at least 2 months before Screening.
12) Abnormal serum electrolytes (potassium, sodium, magnesium) of clinical significance. If treated, must be stably treated for at least 30 days before Screening.
13) Active, acute, or chronic infectious disease of any type.
14) Myocardial infarction or unstable angina within the last 6 months or history of more than one myocardial infarction within 5 years before Screening.
15) Clinically significant (in the judgment of the investigator) cardiac arrhythmia (including atrial fibrillation), cardiomyopathy, or cardiac conduction defect (note: pacemaker is acceptable).
16) Subject has either hypertension not controlled by antihypertensives (supine mean diastolic blood pressure >95 mmHg from 3 sequential measurements), or symptomatic hypotension in the judgment of the investigator.
17) Clinically significant ECG abnormality at Screening as judged by the investigator, including but not limited to a confirmed corrected QT interval using Fridericia's formula (QTcF) value >450 msec for males and >470 msec for females. For QTcF readings that are borderline, and in those where the T and U waves are superimposed or connected, a manual reading should be considered to determine eligibility, in discussion with the Medical Monitor. In subjects with a QRS value >120 msec, those with a QTcF value <500 msec may be eligible following discussion with the Medical Monitor.

18) Positive results of serology screening for hepatitis B (hepatitis B surface antigen [HBsAg]), hepatitis C (anti-hepatitis C virus [HCV] antibodies) or human immunodeficiency virus (HIV) (antibodies type 1 and 2); past history of positive results with cured hepatitis B or hepatitis C may be eligible following discussion with the Medical Monitor and prior approval is required.

19) Chronic kidney disease with estimated glomerular filtration rate (eGFR)<45 mL/min using the Cockcroft and Gault formula with age, sex and weight considered; subject with moderate to severe impairment with eGFR between 44 and 30 mL/min (inclusive) may be eligible following discussion with the Medical Monitor and prior approval is required.

20) Hepatic impairment with alanine aminotransferase (ALT) or aspartate aminotransferase (AST)>2 times the upper limit of normal, or Child-Pugh class B and C.

21) Malignant tumor within 3 years before Screening, except for the following conditions that are stable in the judgement of the investigator:
   a) Adequately treated squamous and basal cell carcinoma, or squamous and basal cell carcinoma in situ
   b) Prostate carcinoma in situ 22) Clinically significant (in the judgment of the investigator) unintentional weight loss within 12 months of Screening.

23) The consumption of grapefruit or grapefruit-containing products is prohibited beginning 7 days prior to the first dose of study medication (Day 1) and during the study.

24) Food supplements and nutraceuticals with potential effects on cognition, such as Axona and medium chain triglyceride (MCT), are prohibited beginning 7 days prior to the first dose of study medication (Day 1) and for the duration of the study.

25) Tetrahydrocannabinol (THC) is prohibited beginning 4 weeks prior to the first dose of study medication (Day 1) and for the duration of the study. Cannabidiol (CBD) without THC is allowed but not on the clinical visit days, except for topical applications.

26) Prohibited prior and concomitant medications are excluded within 4 weeks prior to Screening. All allowed medications should remain stable in terms of dose and regimen throughout the study; for medications affecting cognition, the doses should be stable for at least 4 weeks before Screening and throughout the study, unless otherwise noted. If the permissibility of a specific medication is in question, please contact the Medical Monitor prior to randomization:
   a) Selegiline and trihexyphenidyl in any form or dosage.
   b) Memantine in any form, combination, or dosage.
   c) Donepezil at 23 mg.
   d) Antipsychotics: low doses (in the judgment of the investigator) are allowed if the subject has received a stable dose before Screening. If these medications are taken on a PRN basis they should not be taken the morning before any cognitive testing.
   e) Tryptophan supplements.
   f) Tricyclic antidepressants, irreversible monoamine oxidase B (MAO-B) inhibitors, and S-ketamine; all other antidepressants are allowed only if the subject has received a stable dose for at least 3 months before Screening.
   g) Anxiolytics at high doses; low doses of benzodiazepines are allowed in the judgment of the investigator, but not the night before any cognitive assessments.
   h) Sedative hypnotics; Zolpidem is allowed
   i) Barbiturates (unless given in low doses for benign tremor)
   j) Nicotine therapy (including patches), varenicline (Chantix), or similar therapeutic agent
   k) Peripherally acting drugs with effects on cholinergic neurotransmission, e.g., oxybutinin. Solifenacin is allowed if the subject has received a stable dose for at least 3 months before Screening.
   l) Systemic immunosuppressants if taken in clinically immunosuppressive doses in the judgment of the investigator (note: immunosuppressant use for allergy or other inflammation, e.g., inhaled steroids, otics, opthalmologics, skin creams, and intra-articular injections are allowed).
   m) Antiepileptic medication if taken for control of seizures; other uses, e.g., neuropathy and restless legs, are allowed.
   n) Chronic intake of opioid-containing analgesics; PRN use is allowed (but not within 72 hours before any cognitive assessment).
   o) Sedating $H_1$ antihistamines; PRN use is allowed (but not the night before any cognitive assessment).
   p) Moderate to strong cytochrome P450 3A4 (CYP3A4) inhibitors or inducers.

27) Current enrollment in an investigational drug or device study, or have participated in another clinical trial with an investigational drug within 4 weeks of Screening, or 5 half-lives, whichever is longer, or within 6 months of Screening if an investigational drug for PD or cognition impairment.

28) Subject has known allergy to any component of the ATH-1017 drug product or an allergy to latex.

29) The subject has a condition or is in a situation which, in the investigator's opinion, may put the subject at significant risk, may confound the study results, or may interfere significantly with the subject's compliance or participation in the study.

C. Drug Product

Pre-filled syringes of ATH-1017 at 40 mg contain 1.0 mL of 40 mg/mL ATH-1017 in a solution of 10 mM sodium phosphate and 0.5% NaCl. Pre-filled syringes of ATH-1017 at 70 mg contain 1.0 mL of 70 mg/mL ATH-1017 in a solution of 10 mM sodium phosphate. Each pre-filled syringe of placebo contains 1.0 mL of a solution of 10 mM sodium phosphate and 1.1% NaCl. All solutions are adjusted to pH of approximately 7.6.

ATH-1017 and placebo are administered subcutaneously.

D. Endpoints

The primary objectives and endpoints of this study are:

| Primary Objectives | Primary Endpoints |
| --- | --- |

To evaluate the clinical effects of The Global Statistical Test (GST) (O'Brien, 1984) that ATH-1017 in subjects with PDD combines the scores from cognition (Alzheimer's -continued

| Primary Objectives | Primary Endpoints |
|---|---|
| To determine the safety and tolerability of ATH-1017 in PDD subjects | Disease Assessment Scale-Cognitive Subscale 13-item version [ADAS-Cog$_{13}$]) and change in ERP P300 latency at Week 26 compared to placebo Analysis of adverse events (AEs), including injection site AEs; changes from baseline for the following variables: vital signs, 12-lead electrocardiogram (ECG), and laboratory tests (chemistry, hematology, urinalysis); concomitant medication assessments, physical and neurological exams, Columbia-Suicide Severity Rating Scale (C-SSRS), and Geriatric Depression Scale (GDS) |

The secondary objectives and endpoints of this study are:

| Secondary Objectives | Secondary Endpoints |
|---|---|
| To evaluate the clinical effects of ATH-1017 separately on: (1) cognition and (2) ERP P300 latency | ADAS-Cog$_{13}$ score: change from baseline at Weeks 2, 12, 20, and 26 compared to placebo ERP P300 latency: change from baseline at Weeks 2, 12, and 26 compared to placebo |
| To evaluate the effect of ATH-1017 on activities of daily living | Alzheimer's Disease Cooperative Study-Activities of Daily Living, 23-item version (ADCS-ADL23) score: change from baseline at Weeks 12 and 26 compared to placebo |
| To evaluate the clinical effects of ATH-1017, as determined by the investigator | Clinician Global Impression of Change (CGI-C): change from baseline at Weeks 12 and 26 compared to placebo Clinician Global Impression of Severity (CGI-S): change from baseline at Weeks 12 and 26 compared to placebo |

The exploratory objectives and endpoints of this study include:

| Exploratory Objectives | Exploratory Endpoints |
|---|---|
| To evaluate the clinical effects of ATH-1017, as determined by the caregiver | Caregiver Global Impression of Change (CaGI-C): change from baseline at Weeks 12 and 26 compared to placebo |
| To determine the plasma PK profile of ATH-1017 and ATH-1001 | Day 1: post-dose (anytime between 30 minutes and 120 minutes, as practical) Weeks 12 and 26: pre-dose (anytime) and post-dose (anytime between 30 minutes and 120 minutes, as practical) Note: actual times of PK sampling will be recorded. |
| To evaluate the effect of ATH-1017 on motor function and disease severity | Movement Disorder Society-Unified Parkinson's Disease Rating Scale (MDS-UPDRS) score: change from baseline at Weeks 12 and 26 compared to placebo |
| To evaluate the effect of ATH-1017 on behavioral changes | Non-Motor Symptom Scale (NMSS): change from baseline at Weeks 12 and 26 compared to placebo |
| To further evaluate the effects of ATH-1017 on ERP P300 latency | Persistence of change in ERP P300 latency at Week 30 |
| To further evaluate the effects of ATH-1017 on cognitive ability | Mini-Mental State Examination (MMSE) score: change from baseline at Weeks 12 and 26 compared to placebo |
| To evaluate the effect of ATH-1017 on executive memory function | Controlled Oral Word Association test (COWAT) score: change from baseline at Weeks 12 and 26 compared to placebo |

E. Methods of Assessment
Screening Assessments
1. Montreal Cognitive Assessment (MOCA)

The MOCA was designed as a rapid screening instrument for mild cognitive dysfunction. It assesses different cognitive domains: attention and concentration, executive functions, memory, language, visuoconstructional skills, conceptual thinking, calculations, and orientation.

The total possible score is 30 points; a final total score of 26 and above is considered normal.

The MOCA is administered at Screening only; a score of 11 to 23 inclusive is required to meet the subject eligibility criterion.

Clinical Effect Variables

As specified by each assessment scale, a qualified, trained and certified rater administers questionnaires to the study subject and/or dedicated support person/caregiver. Rater training and certification (as applicable) will occur, and if necessary be repeated, in a standardized manner.

ADAS-Cogn, MMSE, COWAT, and MDS-UPDRS assessments should be done in the same time frame at all visits, in the morning.

1. Cognitive Variables

Alzheimer's Disease Assessment Scale—Cognitive Subscale, 13-Item Version (ADAS Cog13)

The ADAS-Cog$_{13}$ is designed to measure cognitive symptom change in subjects with MCI as well as AD (Mohs, 1997). In addition to the standard 11 items present in the ADAS-Cog$_{11}$ (word recall, commands, constructional praxis, naming objects and fingers, ideational praxis, orientation, word recognition, spoken language ability, comprehension of spoken language, word-finding difficulty, and remembering test instructions), the ADAS-Cog$_{13}$ includes a test of delayed word recall and a number cancellation task. The test comprises 9 performance items and 4 clinician-rated items, with a total score ranging from 0 (no impairment) to 85 (severe impairment). Therefore, higher scores indicate more severe cognitive impairment.

Due to known circadian fluctuations of cognitive capacity (Hilt, 2015), ADAS-Cog$_{13}$ are assessed in the morning at approximately the same time of day as the baseline assessment for all applicable visits.

ADAS-Cog$_{13}$ assessments are performed pre-dose at Visit 2b (Baseline/Day 1), and post-dose), and post-dose at Visit 3 (Week 2), Visit 5 (Week 12), Visit 7 (Week 20), and Visit 8/ET (Week 26).

Mini-Mental State Examination (MMSE)

The MMSE (Folstein, 1975) is a widely used test of overall cognitive function, assessing memory, orientation and praxis in a short series of tests. The score is from 0 to 30 with 30 being the best possible and 0 being the worst possible score.

MMSE assessments are performed pre-dose at Visit 2b (Baseline/Day 1), and post-dose at approximately 1 hour (±30 minutes) at Visit 5 (Week 12), and Visit 8/ET (Week 26).

Controlled Oral Word Association Test (COWAT)

The Controlled Oral Word Association Test (COWAT) is an oral verbal fluency test in which the subject is required to make verbal associations to different letters of the alphabet by saying all the words which they can think of beginning with a given letter. Individuals are given 1 minute to name as many words as possible beginning with each of the letters. The procedure is then repeated for the remaining two letters (Benton, 1994; Strauss, 2006). The test score is the total number of different words produced for all 3 letters.

The COWAT are performed adjacent to the ADAS-Cog$_{13}$ assessment, i.e., pre-dose at Visit 2b (Baseline/Day 1), and post-dose at approximately 1 hour (±30 minutes) at Visit 5 (Week 12) and Visit 8/ET (Week 26).

2. Disease Condition

Movement Disorder Society-Unified Parkinson's Disease Rating Scale (MDS-UPDRS)

The MDS-UPDRS is a 50-question assessment of both motor and non-motor symptoms associated with PD (Goetz, 2006) that features sections that require independent completion by subjects and/or their caregivers, and sections to be completed by the clinician. It consists of 4 parts and results in a total summed score:

Part I—Non-motor aspects of experiences of daily living
Part II—Motor experiences of daily living
Part III—Motor examination
Part IV—Motor complications MDS-UPDRS assessments are performed at Visit 2b (Baseline/Day 1), post-dose at Visit 5 (Week 12), and post-dose at Visit 8/ET (Week 26).

Clinician Global Impression of Change (CGI-C)

The CGI-C is a 7-point Likert scale questionnaire (Busner, 2007) rating the degree of change in the subject's overall PDD symptoms since the start of the study on Day 1 that is completed by the investigator. The 7 possible ratings are as follows:

1=Very much improved: almost entirely treated with minimal symptoms, high level function, substantial change
2=Much improved: significant reduction of symptoms but with symptoms remaining, improved level of functioning
3=Minimally improved: marginally better, little-to-no clinical change in clinical status or symptoms, level of care, or functional capabilities
4=No change: symptoms are unchanged
5=Minimally worse: slightly worse without clinical meaning, little change to clinical status or function
6=Much worse: increase in symptoms and decrease in function; clinically significant
7=Very much worse: symptoms are exacerbated and function is lost The initial CGI-C and CGI-S examination that occurs pre-dose at Visit 2b (Baseline/Day 1) is an assessment of the subject's baseline condition. The subsequent CGI-C and CGI-S assessments of change and severity, respectively, are completed post-dose at Visit 5 (Week 12) and post-dose at Visit 8/ET (Week 26).

Alzheimer's Disease Cooperative Study—Activities of Daily Living, 23-item Version (ADCS-ADL23)

The ADCS-ADL23 (Galasko, 1997) is a 23-item assessment of functional impairment in terms of activities of daily living administered to the support person/caregiver. It comprises 23 questions about the subject's involvement and level of performance across items representing daily living. The questions range from basic to instrumental activities of daily living. Each item is rated from the highest level of independent performance to complete loss. The total score range is from 0 to 78, with lower scores indicating greater functional impairment. ADCS-ADL23 assessments are performed pre-dose at Visit 2b (Baseline/Day 1), post-dose at Visit 5 (Week 12), and post-dose at Visit 8/ET (Week 26).

Caregiver Global Impression of Change (CaGI-C)

The CaGI-C is a 5-point Likert scale questionnaire to be completed by the caregiver that describes how the caregiver feels about the change of the subject's overall PD and dementia symptoms. The question and 5 possible ratings are as follows:

Overall, how have the subject's Parkinson's disease/dementia symptoms changed since the Baseline visit:
1=Much better
2=Somewhat better
3=No change
4=Somewhat worse
5=Much worse The CaGI-C is completed pre-dose at Visit 2b (Baseline/Day 1), post-dose at Visit 5 (Week 12), and post-dose at Visit 8/ET (Week 26).

Non-Motor Symptom Scale (NMSS)

The NMSS is a 30-item scale administered to the support person/caregiver to assess a wide range of non-motor symptoms in patients with PD (Chaudhuri, 2007). The NMSS measures the severity and frequency of non-motor symptoms across 9 dimensions: cardiovascular, sleep/fatigue, mood/cognition, perceptual problems, attention/memory, gastrointestinal, urinary, sexual function, and miscellany. The scale can be used for patients at all stages of PD.

Symptoms are assessed over the last month. Each symptom is scored with respect to:

Severity: 0=None, 1=Mild (symptoms present but causes little distress or disturbance to the patient), 2=Moderate (some distress or disturbance to the patient), 3=Severe (major source of distress or disturbance to the patient)

Frequency: 1=Rarely (<1/week), 2=Often (1/week), 3=Frequent (several times per week), 4=Very frequent (daily or all the time).

Individual domain scores and a total score are calculated. A higher score indicates more severe symptoms.

NMSS assessments are performed pre-dose at Visit 2b (Baseline/Day 1), post-dose at Visit 5 (Week 12), and post-dose at Visit 8/ET (Week 26).

Pharmacodynamic Variables

Pharmacodynamic variables include ERP P300 assessments performed over approximately 10 minutes.

ERP P300 is performed at the Pre-baseline visit (Visit 2a, Day—10 to Day—3, no dosing). ERP P300 data should be uploaded for quality check immediately after the completion of the Pre-baseline visit (Visit 2a).

At Baseline/Day 1 (Visit 2b), ERP P300 is performed at pre-dose following the completion of baseline assessments of MMSE and ADAS-Cogn, and before the CGI-C assessment, up to 1.5 hour before dose in clinic. ERP P300 is assessed post-dose at approximately 2 (±1) hours after ATH-1017 dosing.

At Visits 3, 5, and 8, ERP P300 is performed at pre-dose up to 1 hour before dose in clinic. ERP P300 is assessed post-dose following the completion of ADAS-Cog$_{13}$ assessments, and before the CGI-C/CGI-S assessments, at approximately 2 (±1) hours after IMP dosing.

ERP P300 is also performed at the Safety follow-up visit (Visit 9, no dosing).

ERP P300

ERP P300 is a method of recording brain activity elicited by external stimuli, e.g., an oddball auditory stimulus, and is a well-established functional biomarker, particularly of working memory access (Ally, 2006). ERP P300 is characterized by a stereotyped series of voltage deflections occurring after the respective odd tone to be counted, with early features (<100 msec) corresponding to unconscious sensory transmission (auditory cortex, N100), and later features produced by cognitive processing in the ventral attentional network, i.e., P300, referring to the large positive deflection at roughly 300 msec in healthy adults (young or elderly). The P300 latency is sensitive to detecting reduced synaptic transmission related to cognitive decline in AD patients and other dementias (Olichney, 2011).

To assess the P300 wave (latency and amplitude), the subject is in a sitting position, eyes closed, and has to perform a task related to auditory stimuli. The stimulus consists of an oddball paradigm with 2 sound stimuli. Stimuli are presented through headphones and auditory stimulation for P300 are assessed in a recording lasting up to 10 minutes.

F. Schedule and Order of Assessments

The study consists of up to 24 days of Screening (Day—28 through Day—4), a Pre-baseline visit (Visit 2a, Day—10 to Day—3), Baseline (Visit 2b, Day 1, randomization), followed by 26 weeks of double-blind treatment, and a 4-week safety follow-up. Note: if 24 days is not sufficient to complete the screening period, the possibility of an extension can be discussed with the Medical Monitor.

For clinical outcome assessment evaluating subject's cognitive condition, the general order should be followed:

(1) MM SE
(2) ADAS-Cog13
(3) COWAT
(4) ERP P300 assessments

MMSE assessments are performed first before all other clinical outcome assessments, pre-dose at Baseline/Day 1 (Visit 2b) and post-dose at approximately 1 hour (±30 minutes) at Week 12 (Visit 5), and Week 26 (Visit 8).

ADAS-$Cog_{13}$ and COWAT assessments occur at clinic visits in the morning at approximately the same time they were performed during the initial Baseline/Day 1 assessment. ADAS-$Cog_{13}$ and COWAT assessments are performed pre-dose at Baseline/Day 1 (Visit 2b), and post-dose at approximately 1 hour (±30 minutes) at Week 2 (Visit 3), Week 12 (Visit 5), and Week 26 (Visit 8). Additionally, ADAS-$Cog_{13}$ is assessed at Week 20 (Visit 7).

MDS-UPDRS assessments are organized at adjacent times after the individual ERP P300 assessments at Baseline/Day 1 (Visit 2b), and post-dose at Week 12 (Visit 5), and Week 26 (Visit 8).

PK plasma samples are collected at post-dose at Baseline/Day 1 (Visit 2b); pre-dose and post-dose at Week 12 (Visit 5) and Week 26 (Visit 8). The pre-dose PK sample is collected any time before dosing. The post-dose PK sample is collected anytime between 30 minutes and 120 minutes after dosing as practical. The actual time of dosing and of PK sampling will be recorded.

With the exception of C-SSRS, the order of assessments for all other endpoints (CGI-C, CGI-S, CaGI-C, ADCS-ADL23, NMSS, and GDS) is flexible. The C-SSRS must be completed pre-dose at Baseline/Day 1 (Visit 2b) as part of the eligibility criteria; the order of this assessment is flexible at post-baseline visits.

G. Statistical Methods

A statistical analysis plan (SAP) is issued, providing detailed methods for the analyses outlined below.

Populations for Analysis

MITT population

The modified intent-to-treat (mITT) population includes all randomized subjects who took at least one dose of the study medication and who completed both an ADAS-Cog13 and ERP P300 assessment at Baseline and during at least one post-baseline visit. Subjects are analyzed according to the dose they were randomized to.

Per Protocol Population

The per protocol population includes all mITT subjects who took the assigned medication during the 26 weeks of treatment, completed both an ADAS-$Cog_{13}$ and ERP P300 assessment during at least one post-baseline visit, and did not have any major protocol deviations. Subjects are analyzed based on actual treatment received.

Safety Population

The safety population includes all randomized subjects who received at least one dose of the study medication. Subjects are analyzed based on actual treatment received.

General Considerations

Descriptive statistics for continuous variables include number of subjects (n), arithmetic mean, standard deviation, median, minimum, maximum and first and third quartile limits unless otherwise noted. Frequency and percentage are calculated for categorical variables.

Change from baseline is calculated by subtracting the baseline score from the observed value at any subsequent visit. For safety summaries, the last pre-randomization measurement is defined as the baseline value. For efficacy measures baseline is defined as the last pre-randomization measurement.

Percentages are based on the number of subjects in each treatment group in the given population for AE summary tables, and additionally overall for medical history, prior and concomitant medications. For all other tables, percentages are based on the number of subjects with non-missing data in each treatment group and overall for the given population.

Clinical Efficacy Analyses

Primary Clinical Effect Analysis— GST

The primary efficacy hypothesis is that treatment with ATH-1017 results in a statistically significant reduction in change from baseline in the GST score (O'Brien, 1984) (combining the ADAS-$Cog_{13}$ score and the change from baseline in ERP P300) relative to the placebo group at Week 26 in the mITT population. The primary analysis tests the statistical hypothesis of no difference between placebo and each of the 2 treatment groups (40 mg ATH-1017 and 70 mg ATH-1017).

The primary analysis uses a mixed model for repeated measures (MMRM) to compare the estimated change from baseline between active treatment and placebo in the GST score. This analysis assesses whether or not there is a difference in estimated GST values between treatment groups and placebo at 26 weeks using least squares means estimates from the MMRM model, and includes terms for baseline, baseline by time interaction, and baseline by time by treatment interaction in the model. Additional terms are included for ApoE genotype, site, with smaller sites grouped, age, and MMSE scores. Least squares means and standard errors are estimated from the MMRM model at Week 26. Further details relating to the primary analysis are described in the SAP.

Secondary Analysis— ADAS-Cog13 and ERP P300

The separate secondary variables of ADAS-Cog13 and ERP P300 are analyzed using the same MMRM model that was used for analysis of the primary endpoint.

Additional secondary variables are ADCS-ADL23, CGI-C, and CGI-S; details of analyses are described in the SAP.

Exploratory Analyses

Exploratory variables in this study are: MMSE, COWAT, MDS-UPDRS, NMSS, CaGI-C, and PK; details of analyses are in the SAP.

Subgroup Analyses

Subgroup analyses (e.g., gender, age, GBA genotype) are performed in the mITT population.

H. Interim Analysis

An interim analysis is performed when at least 30 subjects have completed the Week 2 visit. The analysis focuses on the ERP P300 results and is used to determine whether one or other of the 2 active doses of ATH-1017 (40 mg or 70 mg) is superior to the other (difference of 2 standard deviations). If superiority is achieved, then all subsequent subjects enrolled to the study will be assigned to the superior dose until such time as 75 subjects have been enrolled. The subjects on the respective other dose level will continue on their originally assigned dose for the remainder of the trial.

I. Results

Treatment with ATH-1017 achieves one or more of the primary, secondary, or exploratory endpoints, while having acceptable safety and tolerability.

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

It is to be understood that while the disclosure has been described in conjunction with the above embodiments, that the foregoing description and examples are intended to illustrate and not limit the scope of the disclosure. Other aspects, advantages and modifications within the scope of the disclosure are apparent to those skilled in the art to which the disclosure pertains.

REFERENCES

Aarsland, D., and Kurz, M. W. (2010a). The epidemiology of dementia associated with Parkinson's disease. Brain Pathol. 20, 633-639.

Aarsland, D., et al. (2010b). Mild cognitive impairment in Parkinson disease: a multicenter pooled analysis. Neurology 75, 1062-1069.

Ally, B. A., et al. (2006). The P300 component in patients with Alzheimer's disease and their biological children. Biol Psychol 72, 180-187.

American Psychiatric Association. (2013). Diagnostic and statistical manual of mental disorders (5th ed.). https://doi.org/10.1176/appi.books.9780890425596.

Benton, A. L., et al. (1994). *Multilingual Aphasia Examination* (3rd ed.). Iowa City, IA: AJA Associates.

Busner, J., and Targum, S. D. (2007). The Global Clinical Impressions Scale: applying a research tool in clinical practice. Psychiatry 4, 28-37.

Buter, T. C., et al. (2008). Dementia and survival in Parkinson disease: a 12-year population study. Neurology 70,1017-1022.

Chaudhuri, K. R., et al. (2007). The metric properties of a novel non-motor symptoms scale for Parkinson's disease: Results from an International pilot study. Mov. Disord. 22, 1901-1911

Duncan, G. W., et al. (2014). Health-related quality of life in early Parkinson's disease: the impact of non-motor symptoms. Mov. Disord. 29, 195-202.

Ebens, A., et al. (1996). Hepatocyte growth factor/scatter factor is an axonal chemoattractant and a neurotrophic factor for spinal motor neurons. Neuron 17, 1157-1172.

Emre M., et al. (2004). Rivastigmine for dementia associated with Parkinson's disease. N. Eng. J. Med. 351, 2509-2518.

Emre M., et al. (2007). Clinical diagnostic criteria for dementia associated with Parkinson's disease. Mov. Disord. 22, 1689-1707.

FDA Guidance for Industry, Drug-Induced Liver Injury: Premarketing Clinical Evaluation, July 2009.

Folstein, M. F., et al. (1975). "Mini-mental state". A practical method for grading the cognitive state of patients for the clinician. J. Psychiatr. Res. 12, 189-198.

Funakoshi, H., and Nakamura, T. (2011). Hepatocyte Growth Factor (HGF): Neurotrophic functions and therapeutic implications for neuronal injury/diseases. Current Signal Transduction Therapy 6, 156-167.

Galasko, D., et al. (1997). An inventory to assess activities of daily living for clinical trials in Alzheimer's disease. The Alzheimer's disease Cooperative Study. Alzheimer's Disease and Associated Disorders, 11, S33-S39.

Goetz C G, Poewe W, Rascol 0, et al. (2004) Movement disorder society task force report on the Hoehn and Yahr staging scale: status and recommendations. Mov Disord. 19:1020-8.

Goetz, C. G., et al. (2007). Movement Disorder Society-sponsored revision of the Unified Parkinson's Disease Rating Scale (MDS-UPDRS): Process, format, and clinimetric testing plan. Mov. Disord. 22, 41-47.

Helv, M. A., et al. (2008). The Sydney multicenter study of Parkinson's disease: the inevitability of dementia at 20 years. Mov. Disord. 23, 837-844.

Hilt, D. C., et al. (2015). Effect of circadian rhythm on cognition testing in a phase 2B mild/moderate Alzheimer's Disease (AD) study. J Prey Alzheimers Dis. 2, P1-41.

Kalia, L. V., and Lang, A. E. (2015). Parkinson's disease. Lancet. 386, 896-912.

Leiser, S. C., et al. (2011). Aligning strategies for using EEG as a surrogate biomarker: a review of preclinical and clinical research. Biochem. Pharmacol. 81, 1408-1421.

Lippa, C. F. et al. (2007). DLB and PDD boundary issues: diagnosis, treatment, molecular pathology, and biomarkers. Neurology 68, 812-819.

Maina, F., and Klein, R. (1999). Hepatocyte growth factor, a versatile signal for developing neurons. Nature Neuroscience 2, 213-217.

McKeith, I., et al. (2004). Dementia with Lewy bodies. Lancet Neurol. 3,19-28.

McKeith, I., et al. (2017). Diagnosis and management of dementia with Lewy bodies: Fourth consensus report of the DLB Consortium. Neurology 89, 88-100.

Moebius, H., et al. (2019). Phase 1 study of NDX-1017: Safety, pharmacokinetics, and pharmacodynamics in healthy volunteers and dementia patients. The Journal of Prevention of Alzheimer's Disease, 6, S22.

Mohs, R. C., et al. (1997). Development of cognitive instruments for use in clinical trials of antidementia drugs: Additions to the Alzheimer's Disease Assessment Scale that broaden its scope. Alzheimer's Disease and Associated Disorders, 11, S13-S21.

Molnarfi, N., et al. (2014). Hepatocyte growth factor: A regulator of inflammation and autoimmunity. Autoimmun Rev. 14, 293-303.

O'Brien, P. C. (1984). Procedures for comparing samples with multiple endpoints. Biometrics 40, 1079-1087.

Olichney, J. M., et al. (2011). Cognitive event-related potentials: Biomarkers of synaptic dysfunction across the stages of Alzheimer's disease. Journal of Alzheimer's Disease 26, 215-228.

Organ, S. L., and Tsao, M-S. (2011). An overview of the c-MET signaling pathway. Ther Adv Med Oncol. 3, S7-S19.

Piguet, F., et al. (2017). Clinical gene therapy for neurodegenerative diseases: Past, Present, and Future. Human Gene Therapy 28, 988-1003.

Postuma, R. B., et al. (2015). MDS clinical diagnostic criteria for Parkinson's disease. Mov. Disord. 30, 1591-1599.

Rocca, W. A. (2018). The burden of Parkinson's Disease: a worldwide perspective. Lancet Neurology 17, 928-929.

Rosen, W. G., et al. (1984). A new rating Scale for Alzheimer's disease. Am J Psychiatry 141, 1356-1364.

Shang, J., et al. (2011). Strong neurogenesis, angiogenesis, synaptogenesis, and antifibrosis of hepatocyte growth factor in rats brain after transient middle cerebral artery occlusion. J. Neurosci. Res. 89, 86-95.

Sheikh, J. I., and Yesavage, J. A. (1986). Geriatric Depression Scale (GDS): Recent evidence and development of a shorter version. Clinical Gerontologist: The Journal of Aging and Mental Health, 5, 165-173.

Strauss, E., et al. (2006). *Compendium of neuropsychological tests: Administration, norms, and commentary* (3rd ed., p. 502). Oxford: Oxford University Press.

Szeto, J. Y. Y., and Lewis, S. J. G. (2016). Current treatment options for Alzheimer's disease and Parkinsons' disease dementia. Current Neuropharmacol. 14, 326-338.

Tyndall, S. J., et al. (2007). Hepatocyte growth factor-induced enhancement of dendritic branching is blocked by inhibitors of N-methyl-D-aspartate receptors and calcium/calmodulin-dependent kinases. J. Neurosci. Res. 85, 2343-2351.

Tysnes, 0.B., and Storstein, A. (2017). Epidemiology of Parkinson's disease. J. Neural. Transm. 124, 901-905.

What is claimed is:

1. A method of treating Parkinson's disease (PD) and/or Lewy body disease or disorder(s) (LBD), comprising administering to a patient in need thereof 40 or 70 mg per day of a compound of formula A19

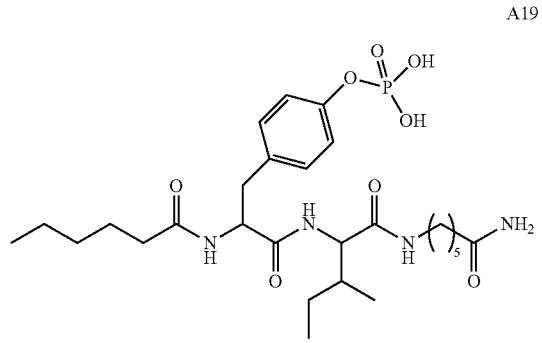

A19 or a pharmaceutically acceptable salt thereof for 26 weeks or more; wherein the patient is acetylcholinesterase inhibitor (AChEI) naive or received an AChEI in the past and discontinued AChEI therapy at least 4 weeks prior to administration of the compound.

2. The method of claim 1, wherein the treating comprises improving one or more symptoms of a motor disorder.

3. The method of claim 1, wherein the patient has been diagnosed with Parkinson's disease dementia (PDD).

4. The method of claim 1, wherein the patient has been diagnosed with Lewy body disease or disorder(s) (LBD).

5. The method of claim 1, wherein the patient is between age 40 and 85.

6. The method of claim 1, wherein the patient is at Hoehn-Yahr stage 1 to 4.

7. The method of claim 1, wherein the compound of formula A19 or the pharmaceutically acceptable salt thereof is administered by subcutaneous injection.

8. The method of claim 1, which slows the decline in the ability to perform activities of daily living and verbal fluency in the patient or improves the ability to perform activities of daily living and verbal fluency in the patient.

9. The method of claim 1, which reduces the rate of decline, stabilizes, or improves a 13-item Alzheimer's Disease Assessment Scale—cognitive subscale (ADAS-Cog13) score.

10. The method of claim 1, which reduces the rate of decline, stabilizes, or improves a Clinician Global Impression of Change (CGI-C) score or a Clinician Global Impression of Severity (CGI-S) score.

11. The method of claim 1, which reduces the rate of decline, stabilizes, or improves an Alzheimer's disease cooperative study-activities of daily living, 23-item version (ADCS-ADL23) score.

12. The method of claim 1, which reduces the rate of decline, stabilizes, or improves a Movement Disorder Society-Unified Parkinson's Disease Rating Scale (MDS-UPDRS) score.

13. The method of claim 1, which reduces the rate of decline, stabilizes, or improves a Non-Motor Symptom Scale (NMSS) score.

14. The method of claim 13, which reduces the rate of decline, stabilizes, or improves a NMSS domain 2 and/or domain 4 score.

15. The method of claim 1, which reduces the rate of decline, stabilizes, or improves a Mini-Mental State Examination (MMSE) score.

16. The method of claim 1, which reduces the rate of decline, stabilizes, or improves a motor symptom in the patient.

17. The method of claim 16, wherein the reduction in the rate of decline, stabilization, or improvement occurs by at least 2 weeks, at least 4 weeks, at least 6 weeks, at least 8 weeks, at least 10 weeks, at least 12 weeks, at least 16 weeks, at least 18 weeks, at least 20 weeks, at least 22 weeks, at least 24 weeks, or at least 26 weeks after the start of treatment.

18. The method of claim 1, comprising administering a monosodium salt of the compound of formula A19.

19. The method of claim 1, comprising administering to the patient in need thereof 40 mg per day of the compound of formula A19, or a pharmaceutically acceptable salt thereof.

20. The method of claim 7, comprising administering to the patient in need thereof 40 mg per day of the compound of formula A19, or a pharmaceutically acceptable salt thereof.

21. The method of claim 9, comprising administering to the patient in need thereof 40 mg per day of the compound of formula A19, or a pharmaceutically acceptable salt thereof.

22. The method of claim 1, wherein the patient has been diagnosed with probable idiopathic Parkinson's disease, or probable LBD.

* * * * *